(12) United States Patent
Shiku et al.

(10) Patent No.: US 8,168,191 B2
(45) Date of Patent: May 1, 2012

(54) CYTOTOXIC T LYMPHOCYTE

(75) Inventors: Hiroshi Shiku, Tsu (JP); Atsunori Hiasa, Tsu (JP); Satoshi Okumura, Tsu (JP); Hiroaki Naota, Tsu (JP); Yoshihiro Miyahara, Tsu (JP)

(73) Assignees: Mie University, Tsu-shi (JP); Takara Bio Inc., Otsu-shi (JP)

( * ) Notice: Subject to any disclaimer, the term of this patent is extended or adjusted under 35 U.S.C. 154(b) by 920 days.

(21) Appl. No.: 12/113,822

(22) Filed: May 1, 2008

(65) Prior Publication Data
US 2009/0068209 A1    Mar. 12, 2009

Related U.S. Application Data

(62) Division of application No. 11/171,365, filed on Jul. 1, 2005, now abandoned.

(30) Foreign Application Priority Data

Oct. 1, 2004    (JP) ................................. 2004-290785

(51) Int. Cl.
*A61K 39/00*    (2006.01)
*C07K 7/06*    (2006.01)

(52) U.S. Cl. ...................................... 424/185.1; 530/328

(58) Field of Classification Search .................. None
See application file for complete search history.

(56) References Cited

U.S. PATENT DOCUMENTS 7,001,999 B1 *    2/2006    Martelange et al. ......... 536/23.5
2005/0249743 A1    11/2005   Boon-Falleur et al.

FOREIGN PATENT DOCUMENTS

WO    WO-03040165 A2    5/2003

OTHER PUBLICATIONS

Stephanie Graff-Dubois et al.; The Journal of Immunology; vol. 169, pp. 575-580, 2002.
Akikhiro Kondo et al.; The Journal of Immunology, vol. 155, pp. 4307-4312, (1995).
Yutaka Kawakami et al.; Proc. Natl. Acad. Sci., vol. 91, pp. 3515-3519, Apr. 1994.
Esteban Celis at al.; Proc. Natl. Acad. Sci., vol. 91, pp. 2105-2109, Mar. 1994.
Beatrice Gaugler et al.; J. Exp. Med., vol. 179, pp. 921-930, Mar. 1994.
James G. McArthur et al.; Journal of Immunotherapy, vol. 21, No. 1, pp. 41-47, 1998.
Hiroaki Naota; Induction and Analysis of CD8+ CTL . . . ; (Mie Univ. Med. Second Dept. Int. Med.), Cancer Science vol. 95 Supplement (2004).
Gillespie, A. et al., "The potential of melanoma antigen expression in cancer therapy", Canc. Treat. Rev., 1999, vol. 25, pp. 219-227.
Celis, E., "Getting peptide caccines to work: just a matter of quality control?", J. Clin. Invest., 2002, vol. 110, pp. 1765-1768.
Grünebach et al., "Delivery of tumor-derived RNA for the induction of cytotoxic T-lymphocytes," Gene Therapy, vol. 10, pp. 367-374, Mar. 2003.
Korean Office Action for Application No. 10-20050001212 dated May 20, 2010.
Mauri et al., "Antigen-presenting T cells induce the development of cytotoxic CD4+ T Cells. I. Involvement of the CD80-CD28 adhesion molecules," J. Immunol., vol. 155, pp. 118-127, Jul. 1, 1995.
Atanackovic et al., "Monitoring CD4+ T Cell Responses Against Viral and Tumor Antigens Using T Cells as Novel Target APC", Journal of Immunological Methods, vol. 278, 2003. pp. 57-66.
Bonehill et al., "Messenger RNA-Electroporated Dendritic Cells Presenting MAGE-A3 Simultaneously in HLA Class I and Class II Molecules", The Journal of Immunology, vol. 172, 2004, pp. 6649-6657.
Gilboa et al., "Cancer Immunotherapy with mRNA-Transfected Dendritic Cells", Immunological Reviews, vol. 199, 2004, pp. 251-263.
Japanese Office Action for Application No. 2004-290785, dated Jun. 25, 2010.
Vantendeloo et al., "Highly Efficient Gene Delivery by mRNA Electroporation in Human Hematopoietic Cells: Superiority to Lipofection and Passive Pulsing of mRNA and to Electroporation of Plasmic cDNA for Tumor Antigen Loading of . . . ", Blood, vol. 98, No. 1, Jul. 1, 2001, pp. 49-56.
Carlsson et al., "Ex vivo stimulation of cytomegalovirus (CMV)-specific T cells using CMV pp65-modified dendritic cells as stimulators," British Journal of Haematology, 2003, vol. 121, No. 3, pp. 428-438.
Herr, "Identification of naturally processed and HLA-presented Epstein-Barr virus peptides recognized by CD4+ or CD8+ T lymphocytes from human blood," Proc. Natl. Acad. Sci., USA, Oct. 12, 1999, vol. 96, No. 21, pp. 12033-12038.
Office Action in Japanese Application No. 2004-290785 mailed Oct. 12, 2010.
Yoshihiro Miyahara et al.; Identification of a HLA-A2402 Restricted MAGE-A4 Derived CTL Epitope by the Use of HLA-transgenic Micen and mRNA Transduced . . . ; (Mie Univ. Second Dept. Int. Med.) (Jul. 6, 2004).

* cited by examiner

*Primary Examiner* — Michael Burkhart
(74) *Attorney, Agent, or Firm* — Birch, Stewart, Kolasch & Birch, LLP

(57) ABSTRACT

The present invention relates to a T lymphocyte having an activity to induce a T lymphocyte recognizing an antigen and a technique to use the T lymphocyte.

2 Claims, 15 Drawing Sheets

CYTOTOXIC T LYMPHOCYTE

The present nonprovisional application is a divisional of U.S. patent application Ser. No. 11/171,365, filed on Jul. 1, 2005, now abandoned for which priority is claimed under 35 U.S.C. §120, the entire contents of which are incorporated herein by reference. The present application also claims priority under 35 U.S.C. §119 to Japanese Patent Application No. 2004-290785 filed on Oct. 1, 2004, the entire contents of which are hereby incorporated by reference.

BACKGROUND OF THE INVENTION

1. Field of the Invention

The present invention relates to T lymphocytes having an activity of inducing T lymphocytes which recognize an antigen, a method of inducing specific antigen-specific T lymphocytes, use of induced T lymphocytes as a therapeutic agent for cancer or an infectious disease, HLA-A2402-restricted cytotoxic T lymphocytes (CTLs) specific for a tumor-associated antigen, an antigen peptide recognized by the CTL, use of the antigen peptide as a CTL inducer and a therapeutic agent for cancer, and a tetramer formed by tetramerizing MHC/antigen peptide complexes which is useful for detection of the CTL.

2. Discussion of Related Art

Among cytotoxic T lymphocytes (CTLs), there is a CTL capable of recognizing, by a specific T cell receptor (abbreviated hereinafter as "TCR"), a complex wherein an antigen peptide and a major histo-compatibility antigen MHC molecule encoded by a major histo-compatibility gene complex (abbreviated hereinafter as "MHC") are bound to each other, thus injuring cells presenting the complex on the cell surface thereof. The major histo-compatibility antigen MHC molecule, in the case of humans, is called human leukocyte antigen (abbreviated hereinafter as "HLA"). The CTL recognizes and injures only a target cell having the same HLA molecule as in the CTL itself Accordingly, the CTL is called "HLA-restricted CTL".

The cytotoxicity reaction can be generated by:
1) the presence of a CTL having a specific TCR, and
2) the presence of an antigen peptide not only capable of binding to an HLA molecule but also forming a complex recognized by the TCR in order to become an antigen peptide presented by an HLA and recognized by the CTL.

Such antigen peptide is generated, for example, by processing, in an endoplasmic reticulum, of an antigen and the like such as a protein synthesized intracellularly in a mammalian cell, to degrade the antigen and the like into smaller epitope peptides. The antigen peptide is further associated with an HLA molecule and presented on the surface of a cell. I.e., the protein is degraded into peptides consisting of from 8 to 15 amino acid residues in a proteosome complex consisting of many subunits, and some of the generated peptides are transported from the cytosol to an endoplasmic reticulum by a TAP transporter. The peptides, when bound to a class I/β2 microglobulin heterodimer in the endoplasmic reticulum, are stabilized as a 3-molecule complex and transported through a Golgi apparatus into the surface of a cell.

Furthermore, it has been revealed that upon infection with organisms such as viruses, microorganisms, protozoa and fungi, a CTL against an antigen possessed by these organisms plays an important role in protection against infection.

The HLA class I molecules are roughly divided into HLA-A, HLA-B and HLA-C. It is known that an antigen peptide presented upon binding to the HLA class I molecule is composed of from 8 to 10 amino acid residues and has certain structural features which vary depending on the respective HLA molecules. For example, a peptide consisting of from 9 to 10 amino acid residues having a Leu residue at the second position from the N-terminal thereof and a Leu residue or a Val residue at the C-terminal is best known worldwide as a peptide binding to the HLA-A2.1 molecule found most frequently. A peptide consisting of from 9 to 10 amino acid residues having any one of a Tyr residue, a Phe residue, a Met residue and a Trp residue at the second position from the N-terminal thereof and any one of a Leu residue, an Ile residue, a Trp residue and a Phe residue at the C-terminal is best known as a peptide binding to an HLA-A24 molecule abundant in Asians races including Japanese (J. Immunol., 155, p. 4307-4312 (1995)).

Tumor antigens of which antigen peptides have been identified up to now include MAGE-1 and MAGE-3 against HLA-AL; MAGE-3, MART1, tyrosinase, gp100, HER2/neu, CEA and the like against HLA-A2.1; MAGE-3 against HLA-Cw1; MAGE-3 against HLA-B44; MAGE-A4 against HLA-B37; MAGE-1, MAGE-2, MAGE-3, CEA, HER2/neu, tyrosinase and β-catenin against HLA-A24, and the like.

Many of the antigen peptides have been found by establishing a tumor cell-recognizing class I-restricted CTL, to identify a tumor antigen recognized by the CTL, finding the minimum unit in a protein serving as the tumor antigen by a genetic engineering method and selecting a peptide in the minimum unit, on the basis of information on a binding motif to HLA class I molecule (*Proc. Natl. Acad. Sci. USA*, 91, p. 3515-3519 (1994)).

The antigen peptide is determined by finding HLA class I molecule-binding peptides consisting of a sequence in a tumor antigen protein, on the basis of a motif structure common in the HLA class I molecule-binding peptide, selecting a CTL-inducible peptide from the found HLA class I molecule-binding peptides, by using antigen-presenting cells, and evaluating whether a CTL having cytotoxicity on tumor cells can be finally induced or not (*Proc. Natl. Acad. Sci. USA*, 91, p. 2105-2109 (1994); *J. Exp. Med.*, 179, p. 921-930 (1994)).

The HLA class I molecules are classified into some subtypes. The subtype possessed by humans varies significantly among races. The proportion of humans having HLA-A2 is highest in the world and accounts for 45% of the Caucasoid, for example. Identification of the HLA-A2-restricted antigen peptide has advanced most. On the other hand, in the Japanese, the proportion possessing HLA-A2 accounts for 40%. 20% of the Japanese have HLA-A*0201 which is the same subtype as in the Caucasoid, and many of the rest of the Japanese have A*0206. Peptides binding to these subtypes vary depending on the subtype. For example, a mainly studied peptide binding to HLA-A2 is HLA-A*0201. On the other hand, the proportion of the Japanese possessing HLA-A24 accounts for 60% or more. The proportion possessing the HLA-A24 is higher in Asian races than in other races.

The antigen peptide, even if the antigen is the same, varies depending on the type of HLA, and induction of a CTL utilizing the antigen peptide is thus troublesome. To solve this problem, various devices have been made, but satisfactory results have not been obtained yet at present. One of the devices is a method of inducing T lymphocytes by utilizing cells obtained by transducing an antigen gene into antigen-presenting cells derived from a patient himself (autologous). As the antigen-presenting cells, use of B cells, macrophages or dendritic cells, known as professional antigen-presenting cells, have been examined, and a clinical test of using the dendritic cells mainly for vaccine adjuvant and the like is conducted (*J. Immunotherapy*, 21, p. 41-47 (1998)). In these antigen-presenting cells, however, there are some disadvantages that much labor is required to prepare the cells in a necessary amount to induce immunization. In addition, the B cells have the advantage that the cells can be prepared in a large amount by immortalization with EB virus. Owing to use of the virus, however, there is the disadvantage of lacked generality. With respect to the method of introducing the gene, introduction of the gene using a virus vector or a plasmid DNA has the disadvantage of generating a new variant in some cases by insertion of the gene into a chromosome.

SUMMARY OF THE INVENTION

A first aspect of the present invention relates to provide RNA-introduced T lymphocytes which enable induction of cytotoxic T lymphocytes which can recognize an antigen, for example act specifically on organisms causing an infectious disease or tumor cells in individuals, exhibit a therapeutic action on a tumor, causing specific cytolysis of target cells or cells presenting a specific antigen in the individuals, or cause cytokine release reaction. A second aspect of the present invention relates to provide an immune inducer capable of inducing the cytotoxic T lymphocytes or inducing immunity effective against cancer or an infectious disease in the individuals. A third aspect of the present invention relates to provide a method of inducing T lymphocytes, which at least enables induction of T lymphocytes recognizing an antigen of interest. A fourth aspect of the present invention relates to provide a therapeutic agent for cancer or an infectious disease, which acts specifically on organisms causing an infectious disease or tumor cells in the individuals. A fifth aspect of the present invention relates to provide cytotoxic T lymphocytes which enable recognition of an antigen, causing specific cytolysis of target cells or cells presenting a specific antigen, or causing cytokine release reaction, in the individuals. A sixth aspect of the present invention relates to provide an inducer of the cytotoxic T lymphocytes, which enables any one of induction of the cytotoxic T lymphocytes or exhibiting a specific action on organisms causing an infectious disease or tumor cells in the individuals. A seventh aspect of the present invention relates to provide a tetramer for detecting T cell receptors possessed by cytotoxic T lymphocytes, which enables any one of monitoring of the cytotoxic T lymphocytes in the individuals or samples derived from the individuals.

A first embodiment of the present invention relates to RNA-introduced T lymphocytes into which an RNA encoding an antigen of interest is introduced, the RNA-introduced T lymphocytes having an activity of inducing T lymphocytes which recognize the antigen. Such RNA-introduced T lymphocytes include, for example, CD4-positive cells activated by phytohemagglutinin. Such RNA-introduced T lymphocytes have an excellent effect that, for example, cytotoxic T lymphocytes which recognize an antigen can be induced by a simple technique. Here, such cytotoxic T lymphocytes can act specifically on organisms causing an infectious disease or tumor cells in individuals, can exhibit a therapeutic action on a tumor, and can specifically cause cytolysis of target cells or cells presenting a specific antigen, cytokine release reaction and the like, in the individuals.

A second embodiment of the present invention relates to a method of inducing T lymphocytes which recognize the antigen, which comprises using the RNA-introduced T lymphocytes in the first embodiment as antigen-presenting cells to induce T lymphocytes which recognize the antigen. The RNA-introduced T lymphocytes include, for example, CD4-positive cells activated with phytohemagglutinin. In addition, the T lymphocytes which recognize an antigen include, for example, CD 8-positive cytotoxic T lymphocytes. The antigen includes a tumor-associated antigen or an antigen of an infectious microorganism. The RNA includes, for example, an RNA prepared from cancerous tissues. The antigen includes, for example, EBNA3A, CMVpp65 and the like. This induction method exhibits an excellent effect that T lymphocytes recognizing the antigen of interest can be simply induced.

A third embodiment of the present invention relates to an immune inducer, which comprises the RNA-introduced T lymphocytes in the first embodiment. Such immune inducer exhibits an excellent effect that, for example, the cytotoxic T lymphocytes can be induced to induce immunity effective against cancer or an infectious disease in the individuals.

A fourth embodiment of the present invention relates to a therapeutic agent for cancer or an infectious disease, which comprises, as an active ingredient, T lymphocytes obtained by the method of inducing T lymphocytes in the second embodiment. Such therapeutic agent for cancer or an infectious disease exhibits an excellent effect that the agent can act specifically on, for example, organisms causing an infectious disease or tumor cells in the individuals.

A fifth embodiment of the present invention relates to cytotoxic T lymphocytes which recognize cells presenting, on the surfaces of the cells, a complex of a human major histo-compatibility antigen (HLA)-A24-restricted antigen peptide represented by SEQ ID NO: 1 or 2 and an HLA-A24 molecule, or a complex of a functional derivative of the HLA-A24-restricted antigen peptide and an HLA-A24 molecule and which are positive to CD8. Such cytotoxic T lymphocytes exhibit an excellent effect of specific recognition of an antigen. The cytotoxic T lymphocytes of the present invention also exhibit an excellent effect that the cytotoxic T lymphocytes can act specifically on, for example, tumor cells in the individuals, exhibit a therapeutic action on tumor, and cause specific cytolysis of target cells or cells presenting a specific antigen, cytokine release reaction and the like, in the individuals.

A sixth embodiment of the present invention relates to a therapeutic agent for cancer, which comprises the cytotoxic T lymphocytes in the fifth embodiment as an active ingredient. Such therapeutic agent for cancer exhibits an excellent effect that, for example, it can act specifically on tumor cells in the individuals.

A seventh embodiment of the present invention relates to an inducer for the cytotoxic T lymphocytes in the fifth embodiment, which comprises, as an active ingredient, at least one antigen peptide selected from the group consisting of a human major histo-compatibility antigen (HLA)-A24-restricted antigen peptide represented by SEQ ID NO: 1 or 2 and the functional derivative thereof. Such inducer exhibits an excellent effect that, for example, the cytotoxic T lymphocytes can be induced by a simple technique to exhibit a specific action on tumor cells in the individuals.

An eighth embodiment of the present invention relates to a therapeutic agent for cancer, which comprises, as an active ingredient, at least one antigen peptide selected from the group consisting of a human major histo-compatibility antigen (HLA)-A24-restricted antigen peptide represented by SEQ ID NO: 1 or 2 and the functional derivative thereof. Such therapeutic agent for cancer exhibits an excellent effect that, for example, the agent can act specifically on tumor cells in the individuals.

A ninth embodiment of the present invention relates to a tetramer for detecting T cell receptors possessed by the cytotoxic T lymphocytes in the fifth embodiment, which comprises a human major histo-compatibility antigen (HLA)-A24-restricted antigen peptide represented by SEQ ID NO: 1 or 2 or the functional derivative thereof. Such tetramer exhibits an excellent effect that, for example, the tetramer can monitor the cytotoxic T lymphocytes in the individuals.

According to the present invention, there is provided a method of inducing a CTL, wherein easily obtainable T lymphocytes are used as antigen-presenting cells. Further, there is provided a novel HLA-A24-restricted antigen peptide. The CTL induced by using the antigen-presenting cells or the antigen peptide is useful, for example, in treatment of cancer.

BRIEF DESCRIPTION OF THE DRAWINGS

FIG. 1A shows the results of EBNA3A, FIG. 1B shows the results of MAGE-A4, and FIG. 1C shows the results of SAGE.

FIG. 4A is a graph showing the results of IFN-γ ELISPOT assay using human bulk CTL cells obtained by sensitization twice with autologous CD4+ PHA blast cells into which SAGE mRNA was introduced. In FIG. 4A, the black bar indicates the results where T2A24 cells pulsed with SAGE$_{715-723}$ peptide were used as target cells, and the shaded bar indicates the results where T2A24 cells pulsed with a control peptide (HER2$_{63-71}$) were used. FIG. 4B is a graph showing the results of expansion of bulk CTLs in well #2. FIG. 4C is a graph showing the results of IFN-γ ELISPOT assay using human bulk CTL cells obtained by sensitization twice with autologous CD4+ PHA blast cells into which SAGE mRNA was introduced.

FIG. 5A is a graph showing the results of staining with SAGE$_{715-723}$ A24 tetramer. FIG. 5B is a graph showing the amount of IFN-γ released by SAGE$_{715-723}$-specific CTL #22 cells in the presence of various cells. FIG. 5C shows the cytotoxicity of SAGE$_{715-723}$-specific CTL #22 cells on various cells. In FIG. 5C, panel A shows K562 cells not expressing SAGE or HLA-A2402. In panel A, the lozenge shows K562 cells, the black square shows K562A24 cells, and the black triangle shows K564A24 pulsed with SAGE$_{715-723}$. Panel B shows R27 cells expressing SAGE but not expressing HLA-A2402. In panel B, the lozenge shows R27 cells, the black square shows R27A24 cells, and the black triangle shows 17A24 pulsed with SAGE$_{715-723}$. Panel C shows LCL not expressing SAGE but expressing HLA-A2402. In panel C, the black triangle shows LCL into which SAGE mRNA was introduced, and the lozenge shows LCL into which EBNA3A mRNA was introduced.

DETAILED DESCRIPTION OF THE INVENTION

Figure 1A:
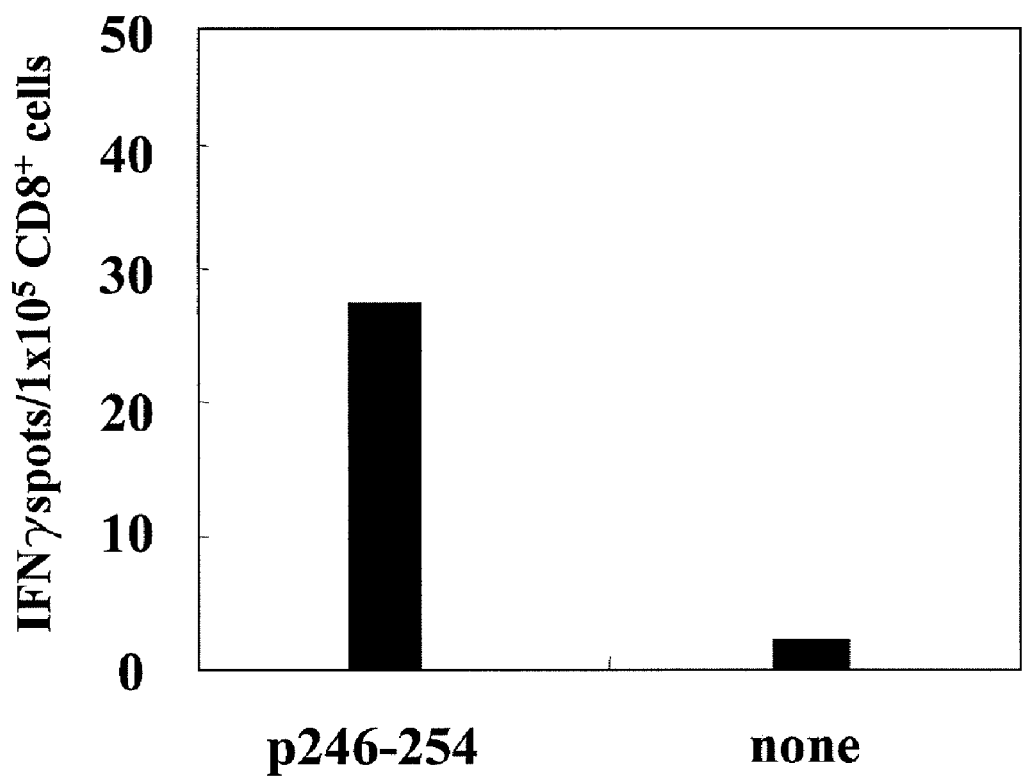
FIGS. 1A to 1C are graphs showing immunogenicity of peptides in HHDA2402+/−β2m−/− mice.

In the present specification, the amino acid residue is sometimes expressed in three-letter or one-letter designation of an amino acid in accordance with conventional nomenclature in biochemistry.

The first embodiment of the present invention relates to RNA-introduced T lymphocytes into which an RNA encoding an antigen of interest is introduced and having an activity of inducing T lymphocytes recognizing the antigen. The RNA-introduced T lymphocytes of the present invention have RNA encoding an antigen of interest introduced into them, and thus exhibit an excellent effect that T lymphocytes recognizing the antigen can be obtained. Accordingly, the RNA-introduced T lymphocytes exhibit an excellent effect that cytotoxic T lymphocytes acting specifically on organisms causing an infectious disease or tumor cells in individuals, exhibiting a therapeutic action on tumors, and causing specific cytolysis of target cells or cells presenting a specific antigen, and cytokine release reaction, in the individuals can be induced by a simple method.

The RNA-introduced T lymphocytes of the present invention can be prepared for example by introducing an RNA encoding an antigen of interest into T lymphocytes derived from natural origin.

The "T lymphocytes derived from natural origin" includes, for example, CD3-positive cells derived from individuals. The "T lymphocytes derived from natural origin" can be identified by using, for example, a monoclonal antibody against CD3 and, if necessary, a monoclonal antibody against a T cell antigen receptor. Such CD3-positive cells may also be CD4-positive and/or CD8-positive cells. The CD3-positive cells are preferably CD4-positive.

The "antigen" includes, but not limited particularly to, tumor-associated antigens, antigens of infectious microorganisms, and the like.

The "tumor-associated antigens" include MAGE (melanoma-associated antigen) family protein, SAGE (sarcoma antigen), LAGE (L antigen), NY-ESO-1, WT-1, hTERT, and the like.

The "antigens of infectious microorganisms" include antigens of EB virus such as EBNA-3A, antigens of cytomegalovirus such as CMVpp65, herpes virus antigen, influenza virus antigen, HIV antigen, *Salmonella* antigen, *Shigella* antigen, *Enterobacter* antigen, protozoa-derived antigen, fungus-derived antigen, and the like.

The RNA may be an RNA prepared by usual genetic engineering techniques, or an RNA prepared from cells. The RNA can be obtained, for example, by extracting an RNA encoding an antigen of interest from cells, reverse-transcribing the resulting RNA into cDNA, amplifying the resulting cDNA by PCR, and carrying out transcription using the amplified DNA as a template. Such RNA can also be used for preparation of the RNA-introduced T lymphocytes of the present invention.

The method of introducing the RNA into T lymphocytes includes, for example, physical methods such as electroporation, a particle gun method, a calcium phosphate method, a lipofection method and a liposome method; biological techniques using viral vectors such as a retrovirus vector, a lentivirus vector and an adenovirus vector; and the like.

Specifically, the RNA-introduced T lymphocytes of the present invention include, for example, CD4-positive cells activated with phytohemagglutinin.

The second embodiment of the present invention relates to a method of inducing T lymphocytes which recognize an antigen, which comprises using, as antigen-presenting cells (also referred to hereinafter as "APC"), RNA-introduced T lymphocytes into which an RNA encoding the antigen of interest is introduced, to induce T lymphocytes recognizing the antigen. Such induction method is based on findings by the present inventors that an antigen-specific CTL can be induced when autologous lymphocytes are stimulated with a T-cell activator such as phytohemagglutinin and cells into which an RNA encoding an antigen is introduced by electroporation are used as antigen-presenting cells, and on surprising findings by the present inventors that the RNA-introduced T lymphocytes exhibit an ability to present the antigen.

The induction method of the present invention exhibits an excellent effect that since the RNA-introduced T lymphocytes into which an RNA encoding the antigen of interest is introduced are used as antigen-presenting cells, T lymphocytes recognizing the antigen of interest can be simply induced. The induction method of the present invention is also advantageous in that the method is excellent in handling (for example, collection, enlargement etc.) of cells as compared with induction of a CTL with B cells, macrophages or dendritic cells known as professional antigen-presenting cells.

The "RNA encoding an antigen of interest" is exemplified by the similar RNA as illustrated in the first embodiment. Specifically, the RNA includes, for example, an RNA encoding an antigen for which induction of cytotoxic T lymphocytes which specifically recognize the antigen is desired (antigen of interest). The antigen includes, for example, a tumor-associated antigen or an antigen of an infectious microorganism and the like. The antigen of infectious microorganisms includes EBNA3A, CMVpp65 and the like. The RNA includes, for example, an RNA prepared from cancer tissues, and the like.

The method of artificially introducing an RNA encoding an antigen of interest into the RNA-introduced T lymphocytes used as antigen-presenting cells includes, but is not limited particularly to, the physical methods and biological methods described above. By such artificial introduction methods, the RNA can be introduced into T lymphocytes, to express the RNA in the resulting RNA-harboring T lymphocytes.

The T lymphocytes and RNA-introduced T lymphocytes can be maintained, for example, in a medium such as RPMI, AIM-V and X-VIVO10, physiologic saline, and buffer solutions such as phosphate buffered physiologic saline.

In the induction method of the present invention, the RNA-introduced T lymphocytes used as antigen-presenting cells may be CD3-positive cells of an individual itself, for example, a patient himself/herself (autologous T lymphocytes) or CD3-positive cells derived from a donor having the same type of HLA as that of an individual such as a patient. The T lymphocytes, similarly to those in the first embodiment, may be CD4-positive or may be CD8-positive. The RNA-introduced T lymphocytes are preferably CD4-positive T lymphocytes. Here, when the individual is an individual, such as a patient, who has underwent transplantation such as allogeneic hematopoietic stem cell transplantation, the T lymphocytes used can be T lymphocytes of a donor of the transplant.

The RNA-introduced T lymphocytes may be activated preferably with lectin such as phytohemagglutinin (PHA) and concanavalin (ConA) or an anti-CD3 antibody in a medium containing IL-2, IL-7 and the like. Insofar as the activation conditions are usually used conditions, the conditions are not limited particularly. For use as antigen-presenting cells, the RNA-introduced T lymphocytes are treated by gamma ray irradiation or with mitomycin.

Here, in the induction method of the present invention, the RNA-introduced T lymphocytes are preferably CD4-positive cells activated with phytohemagglutinin.

Specifically, the RNA-introduced T lymphocytes in the first embodiment can be used as antigen-presenting cells to induce antigen-recognizing T lymphocytes. The antigen-recognizing T lymphocytes to be induced include CD8-positive cytotoxic T lymphocytes (CTLs) and CD4-positive helper T lymphocytes. The "antigen-recognizing T lymphocytes to be induced" vary depending on a starting material used as a source of T lymphocytes derived from natural origin. The "starting material" includes, for example, peripheral blood mononuclear cells (hereinafter also referred to as "PBMC") collected from blood, and CD S-positive lymphocytes separated from the PBMC by a method using an anti-CD8 antibody and magnetic beads. For example, when the PBMC is used as the "starting material", lymphocytes usually in the form of a mixture of antigen-recognizing CTLs and helper T lymphocytes are obtained. In addition, for example, when CD8-positive cells are used as the "starting material", lymphocytes containing a CTL are obtained.

When the CTL is to be induced in vitro, for example, the RNA-introduced T lymphocytes and a sample excised extracorporeally from a living body having the same type of HLA as in the RNA-introduced T lymphocytes can be used to induce the CTL. The "sample excised extracorporeally" in this specification means a sample such as blood; lymph nodes, spleen and other various organs excised by an operation, and the like. Particularly in the induction method of the present invention, lymphocytes and infiltrating lymphocytes occurring in these samples are preferably used.

For example, when blood is used as the sample, the CTL of interest can be induced by repetitive antigenic stimulation with the T lymphocytes into which an RNA encoding the antigen of interest is introduced, to lymphocytes obtained from PBMC prepared from human blood having the corresponding type of HLA. By cloning, the induced CTL can also be maintained as lymphocytes having stabilized cytotoxicity. For example, the induced CTL can be proliferated by stimulation with feeder cells, antigen, various cytokines, or anti-CD3 antibody.

The activity of the induced "cytotoxic T lymphocytes which recognize an antigen", i.e., the activity of the antigen-specific CTL, can be evaluated in terms of cytotoxicity on target cells as an indicator by measuring a radioactive substance released from the target cells pulsed with a peptide from the CTL inducing antigen and labeled with a radioactive substance and the like. In addition, the activity of the antigen-specific CTL can be evaluated by measuring the incorporation of radioactivity into the CTL in the presence of the antigen-presenting cells pulsed with the antigen peptide, whereby the proliferation reaction of the CTL against the antigen-presenting cells pulsed with the antigen peptide can be determined as an indicator of the activity of the antigen-specific CTL. Each of the target cells or antigen-presenting cells which are transduced with a DNA encoding the antigen or into which an RNA encoding the antigen is introduced can also be used for the above purpose. The antigen-specific CTL can be detected by measuring the amount of cytokines such as GM-CSF and IFN-γ released in an antigen-specific manner from the CTL or the target cells. The antigen-specific CTL can also be confirmed directly by using an antigen peptide/HLA complex labeled with a fluorescent dye and the like. In this case, for example, the CTL can be contacted with a first fluorescent marker coupled with a CTL-specific antibody, and the resulting product can be contacted with an antigen peptide/MHC complex coupled with a second fluorescent marker, to confirm the antigen-specific CTL by detecting the presence of cells labeled with both the first and second fluorescent markers by FACS (fluorescence-activated cell sorting) analysis.

The third embodiment of the present invention relates to an immune inducer comprising the RNA-introduced T lymphocytes in the first embodiment. The immune inducer of the present invention comprises the RNA-introduced T lymphocytes as an active ingredient, and thus exhibits an excellent effect that the "cytotoxic T lymphocytes which recognize an antigen" capable of acting specifically on organisms causing an infectious disease or tumor cells in individuals, exhibiting a therapeutic action on a tumor, and causing specific cytolysis of target cells or cells presenting a specific antigen, and cytokine release reaction, in the individuals, can be induced. The immune inducer of the present invention can induce immunity effective against cancer or an infectious disease in the individuals.

The immune inducer of the present invention is provided in the form of a suspension of the RNA-introduced T lymphocytes in the first embodiment in a pharmaceutically acceptable diluent. Here, the "diluent" means, for example, a medium suitable for storing the RNA-introduced T lymphocytes in the first embodiment, or physiologic saline or phosphate buffered physiologic saline. The medium generally includes, but not limited particularly to, a medium such as RPMI, AIM-V and X-VIVO10. These mediums are easily commercially available.

For the purpose of stabilization and the like, a pharmaceutically acceptable carrier may also be added to the immune inducer of the present invention. Here, in this specification, the carrier includes, for example, human serum albumin and the like.

The content of the T lymphocytes in the first embodiment in the immune inducer of the present invention is desirably $1\times10^4$ cells/milliliter or more, preferably $5\times10^5$ cells/milliliter or more, and $1\times10^8$ cells/milliliter or less, preferably $5\times10^7$ cells/milliliter or less, per type of T lymphocyte.

The immune inducer of the present invention is applied to both administration into a donor of the T lymphocytes ("autologous administration") and administration into another individual having the same type of HLA ("allogenic administration").

When the immune inducer of the present invention is to be administered into humans, the immune inducer of the present invention can be administered subcutaneously, intracutaneously or intravenously by a syringe. Although the amount of the immune inducer of the present invention can be determined suitably depending on body weight, disease state, and the like, it is desired that the number of the RNA-introduced T lymphocytes administered into an adult is usually from $10^6$ to $10^{10}$ cells per type of RNA-introduced T lymphocyte. The above range is a standard and not restrictive. Administration of the immune inducer of the present invention can be repeated until the desired effect is obtained.

The RNA-introduced T lymphocytes contained in the immune inducer of the present invention are T lymphocytes derived from an individual (specifically human) as the subject of administration or T lymphocytes having the same type of HLA as that of an individual as the subject of administration. Therefore, toxicity of the RNA-introduced T lymphocytes is not particularly recognized.

The immune inducer of the present invention exhibits an excellent effect that a CTL recognizing an antigen encoded by an RNA introduced into the RNA-introduced T lymphocytes contained in the immune inducer is induced in an individuals (specifically human) into which the immune inducer is administered.

Accordingly, the pharmacological evaluation of the immune inducer of the present invention can be carried out, for example, by measuring the activity of the CTL induced by the immune inducer of the present invention in terms of cytotoxicity on the target cells, proliferation reaction in the presence of antigen-presenting cells, the amount of antigen-specific cytokines released, and the like.

The T lymphocytes obtained by the induction method in the second embodiment, for example, the CTL, can be used as a therapeutic agent for cancer or an infectious disease. Accordingly, a fourth embodiment of the present invention relates to a therapeutic agent for cancer or an infectious disease, which comprises, as an active ingredient, the T lymphocytes obtained by the induction method in the second embodiment. The therapeutic agent can be formulated pursuant to a therapeutic agent for cancer in a sixth embodiment described below, to use in treatment.

In this specification, the therapeutic agent for cancer is intended to encompass so-called carcinostatics.

Pharmacological evaluation of the therapeutic agent for cancer or an infectious disease of the present invention, for example, in the case of cancer, can be carried out where inhibition of growth of cancer cells, death of cancer cells, induction of cell death of cancer cells or shrinkage of cancer cells observed in examination of the cytotoxicity of the therapeutic agent on cancer cells, or shrinkage or disappearance of a cancer site, or prevention of expansion of the cancer site, upon administration of the therapeutic agent for cancer or an infectious disease into the cancer site or therearound, is used as an indicator of the effect of the therapeutic agent on cancer.

Pharmacological evaluation of the therapeutic agent for cancer or an infectious disease of the present invention, for example, in the case of an infectious disease, can be carried out by using, as an indicator of the effect of the therapeutic agent on an infectious disease, suppression of growth of an organism causing an infectious disease or its cells or death of the organism or its cells in examination of the cytotoxicity of the therapeutic agent on the organism or its cells, or reduction or disappearance of symptoms of an infectious disease, upon administration of the therapeutic agent for cancer or an infectious disease in the present invention into individuals (e.g. humans) with an infectious disease.

A fifth embodiment of the present invention relates to cytotoxic T lymphocytes which recognize cells presenting a complex of a human major histo-compatibility antigen (HLA)-A24-restricted antigen peptide represented by SEQ ID NO: 1 or 2 and an HLA-A24 molecule, or a complex of a functional derivative of the antigen peptide and an HLA-A24 molecule on the surfaces of the cells and which are positive to CD8.

The peptide of an amino acid sequence represented by SEQ ID NO: 1 is an HLA-A24-restricted antigen peptide derived from MAGE-A4. The peptide of an amino acid sequence represented by SEQ ID NO: 2 is an HLA-A24-restricted antigen peptide derived from SAGE. Accordingly, the CTL of the present invention exhibits an excellent property of specifically causing cytolysis or cytokine release reaction of the target cells or antigen-presenting cells.

In this specification, the "functional derivative of the HLA-A24-restricted antigen peptide" means a substance having an ability to form a complex with an HLA-A24 molecule, and the formed complex is recognized by a CTL recognizing a complex of an antigen peptide represented by SEQ ID NO: 1 or 2 and an HLA-A24 molecule. The "functional derivative of the HLA-A24-restricted antigen peptide" is, for example, a peptide having an ability to form a complex with an HLA-A24 molecule, the formed complex being recognized by the CTL of the present invention, wherein the amino acid sequence of the functional derivative is different from the amino acid sequence represented by SEQ ID NO: 1 or 2 by:
1) deletion,
2) substitution with other amino acid residues or amino acid analogues,
3) addition of one or more amino acid residues or amino acid analogues, or
4) a combination thereof
of one or several amino acid residues. The length of the amino acid sequence of the functional derivative is preferably from 9 to 10 residues, but is not limited thereto particularly. The "amino acid analogues" in this specification mean N-acylated amino acids, O-acylated amino acids, esterified amino acids, amide amino acids, alkylated amino acids, and the like.

Insofar as the complex of the HLA-A24-restricted antigen peptide or the functional derivative thereof and the HLA-A24 molecule is recognized by the CTL of the present invention, a formyl group, an acetyl group, a t-butoxycarbonyl (t-Boc) group or the like may be bound to the N-terminal amino group of the antigen peptide or the functional derivative thereof, or to a free amino group of a side chain of an amino acid residue. In addition, insofar as the complex of the HLA-A24-restricted antigen peptide or the functional derivative thereof and the HLA-A24 molecule is recognized by the CTL, a methyl group, an ethyl group, a t-butyl group, a benzyl group or the like may be bound to the C-terminal of the antigen peptide or the functional derivative thereof, or to a free carboxyl group in a side chain of an amino acid residue thereof.

The functional derivative can be identified by using the CTL recognizing a complex of the antigen peptide represented by SEQ ID NO; 1 or 2 and an HLA-A24 molecule. The method of identifying the functional derivative includes, for example, the following methods.

The first method is a method wherein a candidate substance as the functional derivative is mixed with HLA-A24-expressing cells, and the candidate substance not bound to HLA-A24 molecules is washed away, to react the resulting product with the CTL. When candidate-specific cytotoxicity, cytokine release or proliferation reaction is recognized in this method, the candidate substance can be judged to be the functional derivative.

The second method is a method wherein a candidate substance is mixed with cells having an ability to present the antigen, and incubated for an appropriate time, for example, for a time required for the antigen to be incorporated and processed and for the antigen peptide and HLA molecule complex to be presented to the surface of the cell, to react the resulting product with the CTL. When candidate-specific cytokine release or proliferation reaction is recognized in this method, the candidate substance can be judged to be the fictional derivative.

A third method is a method wherein a nucleic acid encoding an amino acid sequence of the candidate substance is bound to an expression vector capable of presenting a peptide on HLA-A24 molecules on cells having an ability to present the antigen described below, and wherein suitable cells are transformed by the resulting recombinant vector, thereby reacting the resulting cells having an ability to present the antigen with the CTL. In such method, when candidate substance-specific cytokine release or proliferation reaction is recognized, the candidate substance can be judged to be the functional derivative.

The functional derivative includes, for example, peptides having an ability to bind to HLA-A24 molecules to give a complex of the peptide and an HLA-A24 molecule recognized by a CTL recognizing a complex of a peptide represented by SEQ ID NO: 1 or 2 and an HLA-A24 molecule, out of peptides having the amino acid sequence of SEQ ID NO: 1 or 2, wherein:
1) a second amino acid residue from the N-terminal is substituted with an amino acid selected from the group consisting of a Tyr residue, a Phe residue, a Met residue and a Trp residue typical of the peptide binding to HLA-A24 molecules and/or
2) the C-terminal amino acid is substituted with an amino acid selected from the group consisting of a Leu residue, an Ile residue, a Trp residue and a Phe residue typical of the peptide binding to HLA-A24 molecules, in order to enhance binding to HLA-A24 molecules. More specifically, the functional derivative is, for example, a peptide wherein the C-terminal amino acid Phe residue is substituted with a Leu residue in the amino acid sequence of SEQ ID NO: 2.

Those peptides which have an ability to bind to HLA-A24 molecules to give a complex of the peptide and an HLA-A24 molecule recognized by the CTL of the present invention, out of those peptides wherein one or several amino acid residues (amino acid residues to be substituted) are substituted with amino acid residues or amino acid analogues similar in side chain to the amino acid residues to be substituted in the amino acid sequence of SEQ ID NO: 1 or 2 are also included.

The "amino acid residues similar in side chain to the amino acid residues to be substituted" refer to other amino acid residue(s) belonging to the same group as an amino acid residue in any one of the following groups 1 to 7:
1. glycine (Gly) residue and alanine (Ala) residue;
2. valine (Val) residue, isoleucine (Ile) residue, leucine (Leu) residue and methionine (Met) residue;
3. asparagine (Asn) residue and glutamine (Gln) residue;
4. aspartic acid (Asp) residue and glutamic acid (Glu) residue;
5. serine (Ser) residue and threonine (Thr) residue;
6. lysine (Lys) residue and arginine (Arg) residue; and
7. phenylalanine (Phe) residue and tyrosine (Tyr) residue.

A sixth embodiment of the present invention relates to a therapeutic agent for cancer, which comprises the CTL in the fifth embodiment as an active ingredient. Since the therapeutic agent for cancer of the present invention comprises the CTL of the present invention, the therapeutic agent for cancer exhibits an excellent effect that the agent can act specifically on tumor cells of individuals, especially Asian races, particularly Japanese.

Particularly, the therapeutic agent of the present invention is useful for treatment of cancer wherein expression of the antigen recognized by the CTL in the fifth embodiment, i.e., MAGE-4 or SAGE, is recognized.

The therapeutic agent for cancer according to the present invention is provided in the form of a suspension of the CTL in a pharmaceutically acceptable diluent.

In this specification, the "diluent" refers to, for example, a medium suitable for storage of the CTL, or physiologic saline, phosphate buffered physiologic saline, and the like.

The medium includes, but is not limited to, for example, RPMI, AIM-V, X-VIVO10 and the like.

For the purpose of stabilization, a pharmaceutically acceptable carrier may also be added to the therapeutic agent for cancer according to the present invention, Here, the carrier includes, for example, human serum albumin and the like.

The content of the CTL in the therapeutic agent for cancer according to the present invention is $1 \times 10^4$ cells/milliliter or more, preferably $5 \times 10^5$ cells/milliliter or more, and $1 \times 10^8$ cells/milliliter or less, preferably $5 \times 10^7$ cells/milliliter or less, per kind of CTL.

When the therapeutic agent for cancer according to the present invention is to be administered to human, the agent can be administered, for example, with a syringe. The dose of the therapeutic agent for cancer according to the present invention can be determined suitably depending on body weight, disease state, and the like of the individual, and the number of CTLs administered into an adult is desirably set to be $1 \times 10^6$ to $1 \times 10^{10}$ cells per kind of CTL. Here, the above range is a standard and not restrictive. The active ingredient CTL is a CTL derived from a human as the subject of administration or a CTL having the same type of HLA as in the human, and thus the toxicity of the therapeutic agent for cancer according to the present invention is not particularly recognized.

Pharmacological evaluation of the therapeutic agent for cancer according to the present invention can be carried out in the same manner as described above.

A seventh embodiment of the present invention relates to an inducer of the cytotoxic T lymphocytes (CTLs) in the fifth embodiment, which comprises a human major histo-compatibility antigen (HLA)-A24-restricted antigen peptide represented by SEQ ID NO: 1 or 2, or its functional derivative, as an active ingredient. The present invention is based on the present inventors' finding that the peptide consisting of an amino acid sequence represented by SEQ ID NO: 1 or 2, identified by the present inventors as the HLA-A24-restricted antigen peptide recognized by an HLA-A24-restricted CTL induced against tumor antigen MAGE-A4 or SAGE, is useful for inducing a CTL from human peripheral blood lymphocytes.

Since the CTL inducer of the present invention comprises the HLA-A24-restricted antigen peptide or the functional derivative thereof as an active ingredient, the CTL inducer of the present invention exhibits an excellent effect that the CTL in the fifth embodiment can be induced by a simple technique. Further, the CTL inducer of the present invention exhibits an excellent effect that an action can be exerted specifically on tumor cells in individuals, especially Asian races, particularly Japanese.

The CTL inducer of the present invention is provided in the form of a suspension of the HLA-A24-restricted antigen peptide or the functional derivative thereof alone or in a mixture thereof with other molecules (helper T cell antigen peptide and/or adjuvant) in physiologic saline or phosphate buffered physiologic saline, or in such a form that the peptide or the functional derivative thereof alone, or in the mixture, can be suspended at use.

The HLA-A24-restricted antigen peptide or the functional derivative thereof used in the CTL inducer of the present invention may be bound covalently to a higher fatty acid or a helper T cell antigen peptide or may be formed into a complex with an HLA-A24 molecule. Desirably, the content of the HLA-A24-restricted antigen peptide or the functional derivative thereof in the CTL inducer of the present invention is 0.01% by weight or more, preferably 0.1% by weight or more and 100% by weight or less, preferably 95% by weight or less, per kind of HLA-A24-restricted antigen peptide or the functional derivative thereof.

The CTL inducer of the present invention can be utilized as an additive for a medium for in vitro proliferation of the CTL of the present invention; in diagnosis of an immune-sensitized state with T lymphocyte proliferation activity, delayed skin reaction or the like as an indicator; and the like.

When the CTL inducer of the present invention is used, for example, as an additive in a medium, it is desirable that the amount of the CTL inducer of the invention used is, in terms of peptide concentration in the medium, 1 ng/milliliter or more, preferably 100 ng/milliliter or more and 100 µg/milliliter or less, preferably 1 µg/milliliter or less, per type of the HLA-A24-restricted antigen peptide or the functional derivative thereof. The medium includes mediums such as serum-containing RPMI or AIM-V.

The effect of the CTL inducer of the present invention on induction of a CTL can be evaluated, for example, by measuring the activity of the CTL induced with the inducer, in terms of cytotoxicity on the target cells, proliferation reaction in the presence of antigen-presenting cells, the amount of antigen-specific cytokines released, or the like.

An eighth embodiment of the present invention relates to a therapeutic agent for cancer, which comprises an HLA-A24-restricted antigen peptide represented by SEQ ID NO: 1 or 2 or the functional derivative thereof as an active ingredient. Since the therapeutic agent for cancer according to the present invention comprises the HLA-A24-restricted antigen peptide or the functional derivative thereof as an active ingredient, the therapeutic agent for cancer according to the present invention exhibits an excellent effect that the agent can act specifically on tumor cells in individuals, especially Asian races, particularly Japanese.

The therapeutic agent for cancer according to the present invention is provided in the form of
1) the antigen peptide alone,
2) a mixture of the antigen peptide and a pharmaceutically acceptable carrier and/or diluent, or
3) the above-mentioned 1) or 2) to which a subsidiary agent was added if necessary.

Here, the carrier includes, for example, human serum albumin and the like.

The diluent includes, for example, a phosphate buffer, distilled water, physiologic saline, and the like.

Furthermore, the subsidiary agent includes pharmaceutically acceptable adjuvants and the like. The adjuvants include, but are not limited to, for example, (a) Freund complete adjuvant, (b) Freund incomplete adjuvant, (c) inorganic gel such as aluminum hydroxide, alum, (d) surfactants such as lysolecithin, dimethyl octadecyl ammonium bromide, (e) polyanions such as dextran sulfate, poly IC, (f) peptides such as muramyl peptide, tuftsin, and (g) monophosphoryl lipid (MPL) A manufactured by Ribi Corporation or functional equivalents thereof.

When the therapeutic agent for cancer according to the present invention is administered into humans, the therapeutic agent for cancer according to the present invention may be administered, for example, subcutaneously, intracutaneously or intravenously with a syringe, or may be administered by transdermal absorption through a mucosa by a method such as spraying.

The content of the HLA-A24-restricted antigen peptide or the functional derivative thereof in the therapeutic agent for cancer according to the present invention is desirably 0.01% by weight or more, preferably 0.1% by weight or more, and 100% by weight or less, preferably 95% by weight, per type of HLA-A24-restricted antigen peptide or the functional derivative thereof.

Desirably, the dose of the therapeutic agent for cancer according to the present invention per adult is, in terms of peptide concentration, 0.1 µg/kg or more, preferably 1 µg/kg or more, and 10 mg/kg or less, preferably 1 mg/kg or less, more preferably 100 µg/kg or less, per type of HLA-A24-restricted antigen peptide or the functional derivative thereof. Here, upon administration into humans, toxicity of the therapeutic agent for cancer according to the present invention is not particularly recognized.

A ninth embodiment of the present invention relates to a tetramer for detecting a T cell receptor possessed by the CTL in the fifth embodiment, which comprises an HLA-A24-restricted antigen peptide represented by SEQ ID NO: 1 or 2 or a functional derivative thereof. Such tetramer binds to TCR possessed by the CTL. The tetramer of the present invention comprises the HLA-A24-restricted antigen peptide or the functional derivative thereof, and thus exhibits an excellent effect that the CTL can be monitored in individuals, especially Asian races, particularly Japanese. The present invention is based on the present inventor's finding that a MAGE-A4- or SAGE-specific HLA-A24-restricted CTL can be detected by a tetramer formed by, with biotin-streptavidin, tetramerizing MHC/antigen peptide complexes prepared from the antigen peptide of SEQ ID NO: 1 or 2.

A CTL is activated to cause various immune reactions, upon recognition of, along with the MHC molecule, the antigen peptide binding to the MHC molecule on the cell surface of an antigen-presenting cell or a target cell by a complex of a T cell receptor (TCR) and a CD3 molecule on the cell surface of the CTL.

According to the tetramer of the present invention, the MHC tetramer can be utilized for a different TCR, i.e., an HLA-A24-restricted antigen peptide from MAGE-A4 or SAGE, and is useful in analysis on behavior or functions of a CTL, particularly for a method of specific measurement of a CTL having the TCR of interest. The tetramer of the present invention can be obtained, for example, by tetramerizing complexes formed from the HLA-A24-restricted antigen peptide of SEQ ID NO: 1 or 2 or the functional derivative thereof, β2 microglobulin and an HLA-A24 molecule by a biotin-streptavidin method.

The tetramer of the present invention binds to a T cell receptor possessed by a CTL, and is thus useful, for example, in that the tetramer can be utilized in a method for measuring a CTL which can be carried out in a short time and is simple, by using the formation of complex of the tetramer and a CTL as an indicator in place of measurement of the cytotoxicity of a CTL. The tetramer of the present invention is useful particularly in detection or separation of a CTL in a sample such as PBMC containing only a small amount of CTL.

The tetramer of the present invention can also be used in ELISPOT (enzyme-linked immunospot) used for monitoring T lymphocytes in the body of a patient, or for target cells in a cytotoxicity test.

The tetramer of the present invention is also useful in monitoring a CTL.

Hereinafter, the present invention will be described in more detail by reference to the Examples, but the present invention is not limited to the Examples.

EXAMPLE 1

Identification of HLA-A2402-Restricted CTL Epitope (Antigen Peptide) Using HLA-A2402 Transgenic Mice (1) Materials and Method
HHDA2402+/−β2m−/− Mice A DNA construct (HHDA2402) containing an HLA-A2402 leader sequence, human β2 microglobulin, HLA-A2402 α1 and α2 domains, an H-2D$^b$ α3 transmembrane domain, and a cytoplasm domain was constructed. The resulting construct was cloned into an expression vector pcDNA 3.1 (manufactured by Invitrogen Corporation). The HHDA2402 construct (4 kb SalI-NotI fragment) was injected into fertilized eggs of C57BL/6 mice, to give HHDA2402-expressing mice. Then, the HHDA2404-expressing mice were bred with β2m−/− mice (manufactured by The Jackson Laboratory). The resulting HHDA2402+/−β2m+/− were bred with β2m−/− mice to give HHDA 2402+/−β2m−/− mice (referred to hereinafter as "HHDA2402 mice").

(2) Cell Strain

TAP transporter-deficient strain T2 (J. Immunol., 167, p. 2529-2537 (2001)) was transfected with an HLA-A2402 cDNA to prepare T2A24 strain. The following cell strains were also used in preparation of CTL target cells: breast cancer cell strain R27 (A2402-negative), esophagus cancer strain KE-4 (A2402-positive), esophagus cancer strain TE-10 (A2402-positive), chronic myelocytic leukemia strain K562 (A2402-negative), lung cancer strain 11-18 (A2402-positive) and embryonic renal cell 293 (A2402-negative). The above-mentioned R27, K562 and 293 were transfected with an HLA-A2402 cDNA to prepare R27A24, K562A24 and 293A24. Hunan B-lymphoblast (LCL) was prepared in a usual manner from HLA-A2402-positive or negative cells derived from volunteers by using EBV.

(3) Plasmid cDNA of the full-length MAGE-A4, SAGE or EBNA-3A was cloned into pcDNA 3.1.

(4) Immunization with a Gene Gun

Using Helios Gene Gun System (trade name, manufactured by Bio-Rad Laboratories, Inc.), gold particles coated with plasmid DNA were administered endoabdominally at a helium pressure of from 350 to 400 psi into HHDA2402 mice (6- to 8-week-old, female). The gold particles were prepared according to a manufacturer's manual. After 2 weeks, booster administration was carried out. After 1 week, spleen cells were collected.

One week after the final immunization, MACS system (trade name, manufactured by Mitlenyi Biotec) using CD8 alpha (Lyt 2) microbeads was used, to select CD8-positive T cells. The purity of the resulting T cell fraction analyzed by flow cytometry was 95% or more.

(6) ELISPOT Assay (Mice)

A 96-well nitrocellulose ELISPOT plate (trade name: MAHA S4510, manufactured by Millipore Corporation) was incubated overnight with 2 µg/milliliter anti-mouse IFN-gamma mAb (trade name: clone R4-6A2, manufactured by PharMingen Company) at 4° C., to coat the plate. Each well was washed with phosphate buffered physiologic saline (PBS). The well after washing was blocked by incubation at 37° C. for 2 hours in FCS-containing RPMI1640 medium.

Fresh CD8-positive cells (1×10$^5$ cells/well) derived from the immunized mice and CD8-negative cells (1×10$^6$ cells/well) pulsed with various peptides were seeded to each well and regulated so as to have a final volume of 200 µl. Then, the cells were cultured at 37° C. for 22 hours. Thereafter, the cells were washed sufficiently with PBS containing 0.05 wt % Tween™ 20 (referred to as "PBS-Tween"). Two hundreds microliters of 1.25 µg/milliliter biotinylated anti-mouse IFN-gamma mAb (trade name, manufactured by PharMingen Company) was added to the cells after washing, and the cells were then cultured overnight at 4° C. The cells thus obtained were washed with PBS-Tween. One hundred microliters of 1 µg/milliliter streptavidin-alkaline phosphatase conjugate (trade name, manufactured by Mabtech Ltd.) was added to the cells after washing. Thereafter, the resulting mixture was incubated at room temperature for 90 minutes, to carry out reaction. The resulting product was washed with PBS-Tween and then stained with an alkaline phosphatase conjugate substrate kit (trade name, manufactured by Bio-Rad Laboratories, Inc.). Thereafter, the product after staining was washed with distilled water to terminate the reaction. Then, the plate was dried and spots were counted.

(7) Estimation of Epitope Peptides

Nine-residue peptide which might have an ability to bind to HLA-A2402 were searched for by using HLA Peptide Binding Predictions running on a web site of BioInformatics & Molecular Analysis Section (BIMAS).

Each of five peptides derived from SAGE and ten peptides derived from MAGE-A4 shown in Table 1 below were chemically synthesized by a peptide synthesizer.

TABLE 1

| Antigen name | Amino acid position | Amino acid sequence |
|---|---|---|
| SAGE | 841-848 | NYERIFILL (SEQ ID NO: 3) |
|  | 776-784 | LYKPDSNEF (SEQ ID NO: 4) |
|  | 715-723 | LYATVIHDI (SEQ ID NO: 2) |
|  | 621-629 | QYAAVTHNI (SEQ ID NO: 5) |
|  | 250-258 | TYNVPEEKM (SEQ ID NO: 6) |
| MAGE-A4 | 239-247 | VYGEPRKLL (SEQ ID NO: 7) |
|  | 143-151 | NYKRCFPVI (SEQ ID NO: 1) |
|  | 271-279 | EFLWQPRAL (SEQ ID NO: 8) |
|  | 151-159 | IFGKASESL (SEQ ID NO: 9) |
|  | 113-121 | KVDELAHFL (SEQ ID NO: 10) |
|  | 283-291 | SYVKVLEHV (SEQ ID NO: 11) |
|  | 124-132 | KYRAKELVT (SEQ ID NO: 12) |
|  | 199-207 | KTGLLIIVL (SEQ ID NO: 13) |
|  | 301-309 | AYPSLREAA (SEQ ID NO: 14) |
|  | 43-51 | SSPLVPGTL (SEQ ID NO: 15) |

Here, the "amino acid position" in the table indicates the position of each peptide in an amino acid sequence of SAGE or MAGE-A4.

Furthermore, similarly, EB virus-derived EBNA $3A_{246\text{-}254}$ (SEQ ID NO: 16, RYSIFFDYM) and HER2-derived $HER2_{63\text{-}71}$ (SEQ ID NO: 17, TYLPTNASL) were synthesized. The purity of the peptides used was 90% or more.

HHDA2402 mice were immunized with an expression plasmid carrying EB virus-derived EBNA 3A gene by a gene gun. After immunized twice, spleen-derived CD8+T cells were prepared. CD8-negative cells pulsed with the EBNA $3A_{246\text{-}254}$ peptide were used as target cells, to carry out ELISPOT assay. The results are shown in FIG. 1A.

As a result, EBNA $3A_{246\text{-}254}$ peptide-specific CTLs were detected as shown in FIG. 1A.

A tumor antigen MAGE-A4-derived candidate peptide and a testis antigen SAGE-derived candidate peptide (Table 1 above) were then subjected to ELISPOT assay in the same manner. The results are shown in FIGS. 1B and 1C.

Figure 1B:
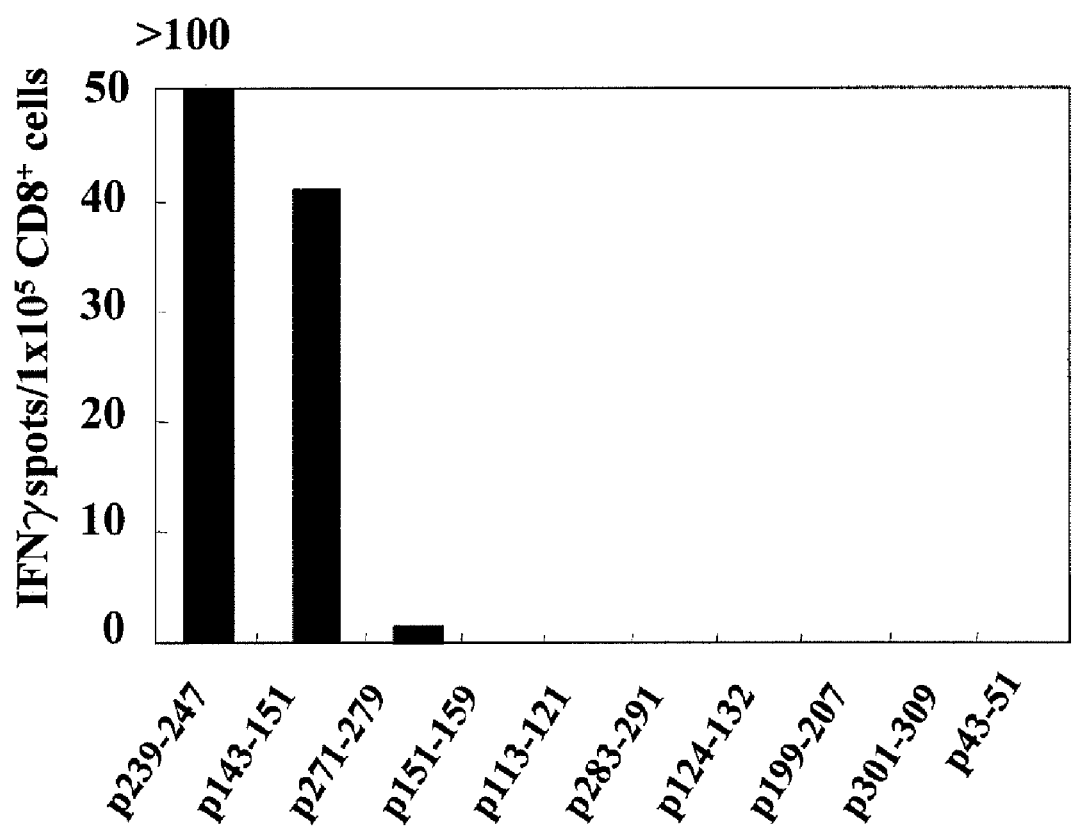
Figure 1C:
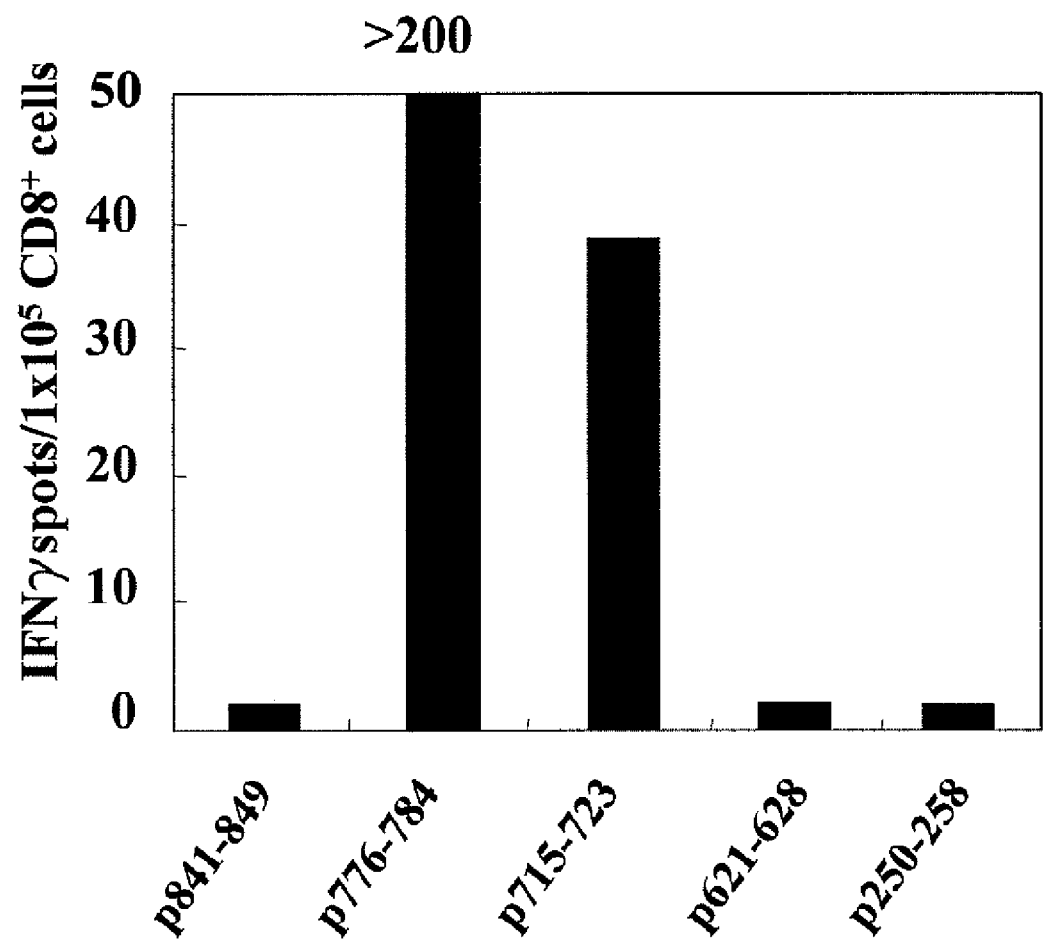

As a result, two peptides ($MAGE\text{-}A4_{239\text{-}247}$ and $MAGE\text{-}A4_{143\text{-}151}$) were positive in MAGE-A4, as shown in FIG. 1B. Similarly, as shown in FIG. 1C, two peptides ($SAGE_{776\text{-}784}$ and $SAGE_{715\text{-}723}$) were positive in SAGE.

Wild-type C57BL6 mice were then used, to conduct the same experiment as above. As a result, only $MAGE\text{-}A4_{239\text{-}247}$ and $SAGE_{776\text{-}784}$ were positive.

Accordingly, $MAGE\text{-}A4_{143\text{-}151}$ and $SAGE_{715\text{-}723}$ were identified as antigen peptides presented by HLA-A2402.

EXAMPLE 2

Preparation of HLA-2402 Antigen Peptide-Specific Human Cytotoxic T Lymphocytes (CTLs) Using CD4-Positive PHA Blast Cells into which mRNA was Introduced (1) Preparation of mRNA MAGE-A4 plasmid and SAGE plasmid were linearized. The resulting products and T7 polymerase (trade name: MMES SAGE mMACHINE T7 Kit, manufactured by Ambion, Inc.) were used, to conduct in vitro transfer according to a manufacturer's manual. Thereafter, the resulting product was polyadenylated with poly A polymerase (trade name: Poly(A) Tailing Kit, manufactured by Ambion, Inc.) according to a manufacture's manual. The resulting RNA was stored at −80° C. until use.

(2) Preparation of CD4-Positive Phytohemagglutinin (PHA) Blast Cells

By using positive selection using MACS CD4 microbeads (manufactured by Miltenyi Biotec), fresh CD4-positive cells were separated from PBMC. The resulting CD4-positive cells were seeded on a 24-well plate (manufactured by Corning Incorporated) at a cell density of from 1 to $2 \times 10^6$ cells/milliliter RPMI-1640 medium (composition: containing 25 mM Hepes, 10 wt % inactivated human AB serum, 2 mM L-glutamine, 100 U/milliliter penicillin, 100 µg/milliliter streptomycin) per well.

On the 0th day, PHA (trade name: HA15, manufactured by Murex S. A.) was added to the medium in each well of the plate at a final concentration of 10 µg/milliliter. On the 3rd day, half amount of the medium was exchanged with the above medium containing IL-2 (20 U/milliliter) and IL-7 (40 ng/milliliter). Exchange of the medium was repeated every 3 days, whereby activated CD4-positive cells were obtained. The mRNA was introduced by electroporation into the activated CD4-positive cells at 14 to 28 days after culture was initiated. The resulting cells were used below as antigen-presenting cells.

(3) In Vitro Induction of Human CTLs Using mRNA-Introduced CD4-Positive Blast Cells MACS CD8 Microbeads (trade name, manufactured by Miltenyi Biotec) were used, to separate CD8+ T cells from PBMC. The number $5 \times 10^5$ cells of CD8+ T cells thus obtained were stimulated with radiation (30 Gy)-irradiated $1 \times 10^5$ RNA-introduced CD4+ PHA blast cells in a 96-well round plate (manufactured by Nunc Corporation). After 7 days, the CD 8+ T cells were stimulated again with radiation (30 Gy)-irradiated $1 \times 10^5$ mRNA-introduced CD4+ PHA blast cells, and then cultured in an IL-2 (20 IU/milliliter)-containing RPMI1640 medium for 7 days.

(4) In Vitro Amplification of CTLs

To amplify the sensitized CD8+ T cell group containing the antigen-specific CTLs, autologous LCLs ($5 \times 10^6$ cells) into which the target antigen mRNA was introduced, autologous PBMCs ($2.5 \times 10^7$ cells), and IL-2 (20 IU/milliliter) were added to the sensitized CD8+ T cell group. The resulting mixture was cultured in the absence of anti-CD3 antibody in a 25-milliliter flask (manufactured by Corning Incorporated).

(5) Limiting Dilution

The CD8+ T cells were diluted to a density of 0.3 cell/well in a 96-well round plate (manufactured by Nunc Corporation). Furthermore, autologous PBMCs ($5 \times 10^4$ cells/well), radiation-irradiated LCLs ($1 \times 10^4$ cells/well), IL-2 (20 IU/milliliter), and anti-CD3 mAb (30 ng/milliliter) were added to the resulting dilution. The resulting mixture was cultured. As a result, CD8+ T cells lyzing the antigen-presenting cells as the target were proliferated in the presence of radiation-irradiated PBMC, radiation-irradiated LCL, and anti-CD3 mAb.

(6) ELISPOT Assay (Human)

A 96-well nitrocellulose ELISPOT plate (trade name: MAHA S4510, manufactured by Millipore Corporation) was coated by overnight incubation at 4° C. with 2 μg/milliliter antihuman IFN-γ mAb (trade name: 1-D1K). Each well was washed with PBS, and then blocked by incubation at 37° C. for 2 hours with RPMI1640 medium containing 10 wt % human AB serum. Effecter cells ($2 \times 10^4$ cells/well) and peptide-pulsed T2A24 cells ($5 \times 10^4$ cells/well) were seeded to each well. The cells in the well were cultured at 37° C. for 18 hours. The resulting cells were washed sufficiently with PBS-Tween. After washing, the cells were incubated overnight with 1.25 μg/milliliter biotinylated anti-mouse IFN-gamma mAb (manufactured by PharMingen Company) at 4° C. The resulting product was washed with PBS-Tween. One hundred microliters of 1 μg/milliliter streptavidin-alkaline phosphatase conjugate (manufactured by Mabtech Ltd.) was added to the resulting product and reacted by incubation at room temperature for 60 minutes. The resulting product was washed with PBS-Tween and then stained with an alkaline phosphatase conjugate substrate kit (trade name, manufactured by Bio-Rad Laboratories, Inc.). The resulting product was then washed with distilled water to terminate the reaction. Then, the plate was dried and spots were counted.

(7) $^{51}$Cr Release Cytotoxicity Assay

The cytotoxicity was evaluated in a usual manner as follows. The target cells were labeled with 100 μCi ($3.7 \times 10^6$ Bq) $^{51}$Cr. Then, $1 \times 10^4$ target cells were reacted in a 96-well V-bottomed plate (manufactured by Nunc Corporation) with effecter cells at various density at 37° C. After 5 hours, 100 μl supernatant was collected and measured for radioactivity. This measurement was conducted in triplicate, and the average of specific lysis % in 3 wells was calculated on the basis of the following formula:

Specific cytotoxic activity (%)=[(measurement of each well−minimum release level)/(maximum release level−minimum release level)]×100

In the above formula, the "minimum release level" is the $^{51}$Cr level of the well containing only the target cells and K562 cells, and indicates the natural release level of $^{51}$Cr from the target cells. The "maximum release level" is indicative of the $^{51}$Cr release level upon disruption of the target cells with surfactant Triton™ X-100 added to the cells.

According to the above-mentioned items (1) to (7), the following evaluation was conducted.

CD8+ cells prepared from healthy normal humans were sensitized in vitro with autologous CD4+ PHA blast cells into which mRNA was introduced. The CD8+ cells were stimulated twice with the autologous CD4+ PHA blast cells into which MAGE-A4 mRNA was introduced. The results of ELISPOT assay are shown in FIG. 2.

Figure 2:
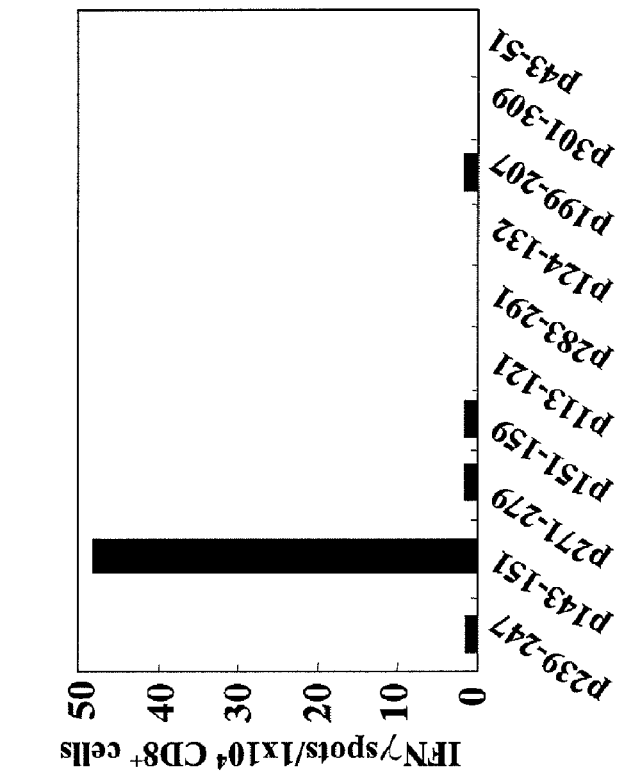
FIG. 2 is a graph showing immunogenicity of MAGE-A4-derived peptides in humans. Panel A is a graph showing the results of IFN-γ ELISPOT assay of human bulk CTLs sensitized twice with autologous CD4+ PHA blast cells into which a mRNA corresponding to MAGE-A4 or SAGE was introduced. In panel A, the black bar indicates LCL into which MAGE-A4. mRNA was introduced, and the shaded bar indicates LCL into which SAGE mRNA was introduced. Panel B is a graph showing the results of expansion of well #2 with autologous LCL into which mRNA corresponding to MAGE-A4 or SAGE was introduced, or with autologous PBMC and IL-2 (20 IU/milliliter).
Figure 2:
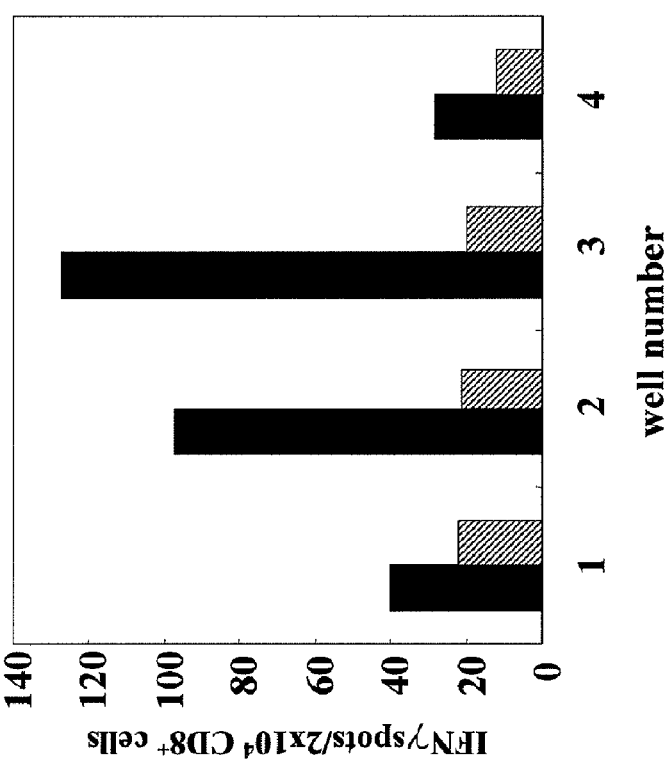

As a result, MAGE-A4-specific bulk CTLs were obtained as shown in panel A in FIG. 2. As shown in panel B in FIG. 2, cells obtained by amplifying the MAGE-A4-specific bulk CTLs with mRNA-introduced autologous LCL, autologous PBMC and IL-2 showed reaction specific to T2A24 cells pulsed with MAGE-A4$_{143-151}$ peptide.

Figure 3:
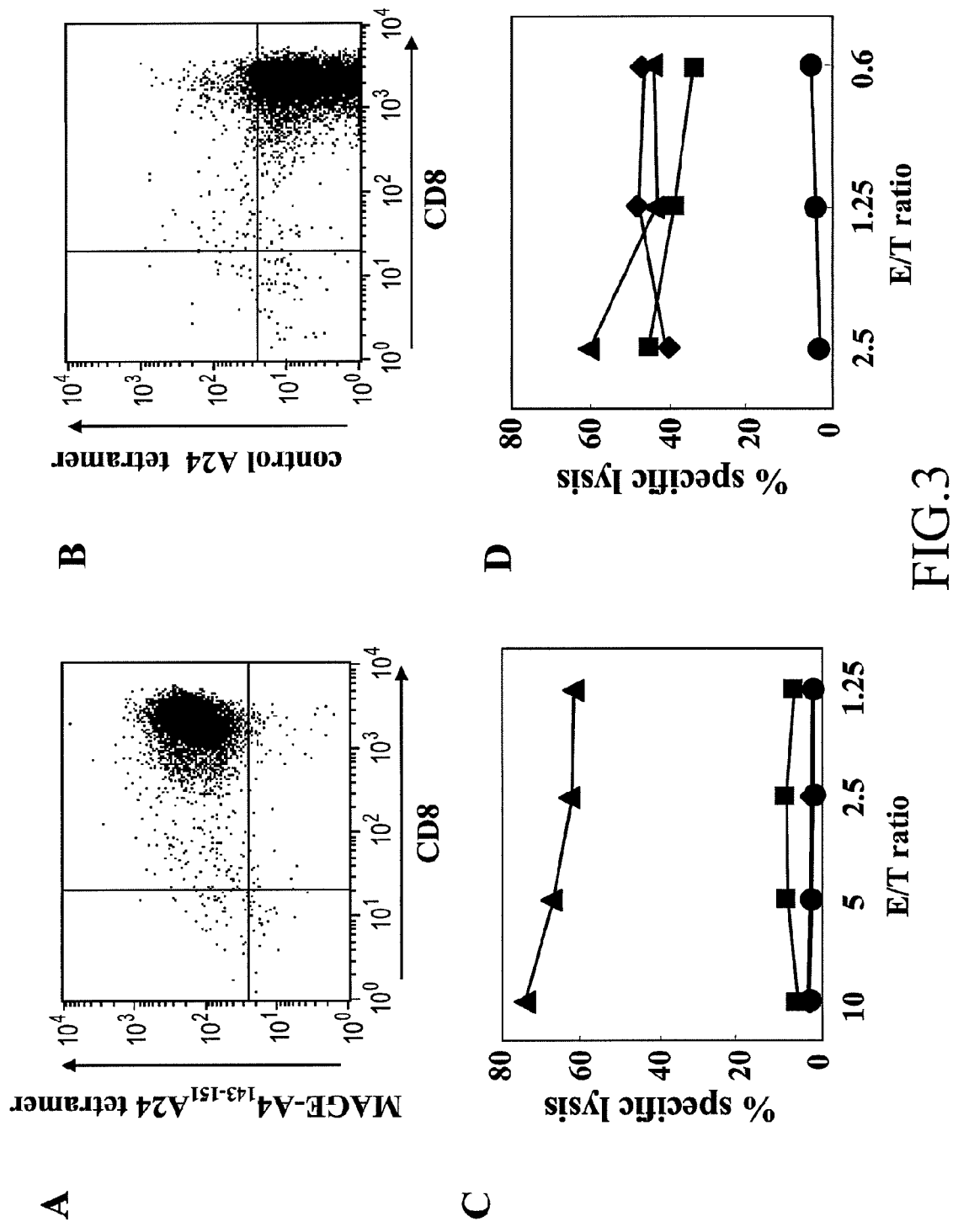
FIG. 3 is a graph showing the results of presentation of cell surfaces with MAGE-A4$_{143-151}$ peptide together with HLA-A2402 after intracellular processing. Panel A shows the result of staining with MAGE-A4$_{143-151}$, A24 tetramer and panel B shows the results of staining with a control tetramer. Panel C shows the cytotoxicity of MAGE-A4$_{143-151}$-specific CTL #2-28 cells on tumor cells. The black triangle shows T2A24 pulsed with MAGE-A4$_{143-151}$; the black square shows T2 pulsed with MAGE-A4$_{143-151}$; the lozenge shows T2A24 pulsed with SAGE$_{715-723}$; and the black circle shows T2A24 not pulsed. Panel D shows the cytotoxicity of MAGE-A4$_{143-151}$-specific CTL #2-28 cells on tumor cells. The black triangle shows KE-4 cells expressing HLA-A2402 and MAGE-A4; the black square shows TE-10 cells expressing HLA-A2402 and MAGE-A4; the lozenge shows 11-18 cells expressing HLA-A2402 and MAGE-A4; and the black circle shows LB-23 cells expressing HLA-A2402, but not expressing MAGE-A4.

Furthermore, MAGE-A4$_{143-151}$-specific #2-28 cells obtained by limiting dilution were analyzed by flow cytometry using MAGE-A4$_{143-151}$ tetramer and anti-CD8 antibody, and the results are shown in panels A and B in FIG. 3. The cytotoxicity by MAGE-A4$_{143-151}$-specific #2-28 cells was examined, and the results are shown in panels C and D in FIG. 3.

As a result, the #2-28 cells obtained by limiting dilution were stained positively with the MAGE-A4$_{143-151}$ tetramer, but not stained with a tetramer used as a control, as shown in panels A and B in FIG. 3. As shown in panel C in FIG. 3, the #2-28 cells showed HLA-A2402-restricted cytotoxicity on the target cells pulsed with the MAGE-A4$_{143-151}$-peptide. Furthermore, as shown in panel D in FIG. 3, the #2-28 cells showed cytotoxicity on the tumor cell strain expressing both MAGE-A4 and HLA-A2402. This indicates that the MAGE-A4$_{143-151}$ peptide is presented not only against the mRNA-introduced CD4+ PHA blast cells but also against the HLA-A2402-positive tumor cells by intracellular processing of MAGE-A4 antigen.

Similarly, human bulk CTL cells were obtained by sensitization twice with SAGE mRNA-introduced autologous CD4+ PHA blast cells. IFN-γ ELISPOT assay was conducted using the resulting human bulk CTL cells. As the target cells, T2A24 cells pulsed with SAGE$_{715-723}$ peptide or T2A24 cells pulsed with the control peptide were used. The results are shown in FIG. 4A.

Figure 4A:
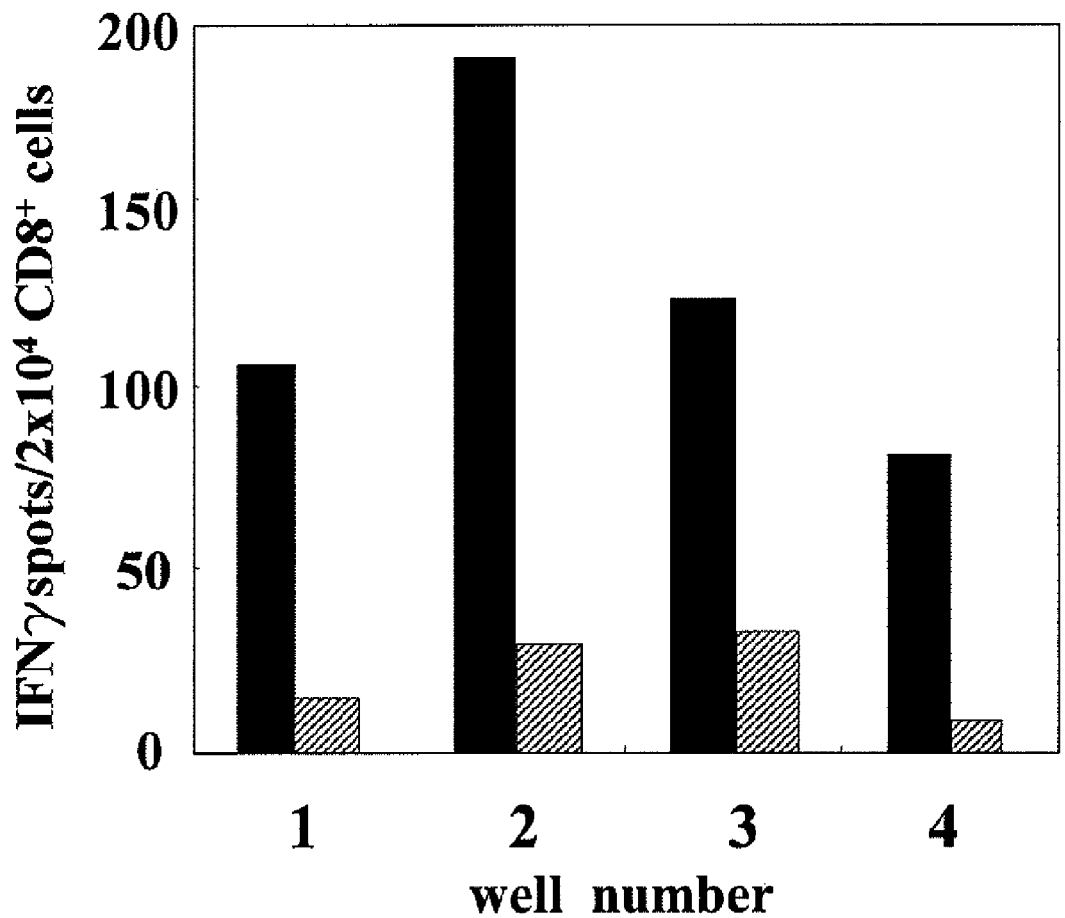
FIGS. 4A to 4C are graphs showing the immunogenicity of SAGE$_{715-723}$ peptide in humans.

As a result, SAGE$_{715-723}$-specific bulk CTLs were inducted by stimulation twice with CD4+ blast cells into which truncated SAGE mRNA was introduced, as shown in FIG. 4A.

The bulk CTLs were amplified in vitro. The resulting CTL was analyzed by flow cytometry using SAGE$_{715-723}$ tetramer and anti-CD8 antibody. The results are shown in FIG. 4B.

Figure 4B:
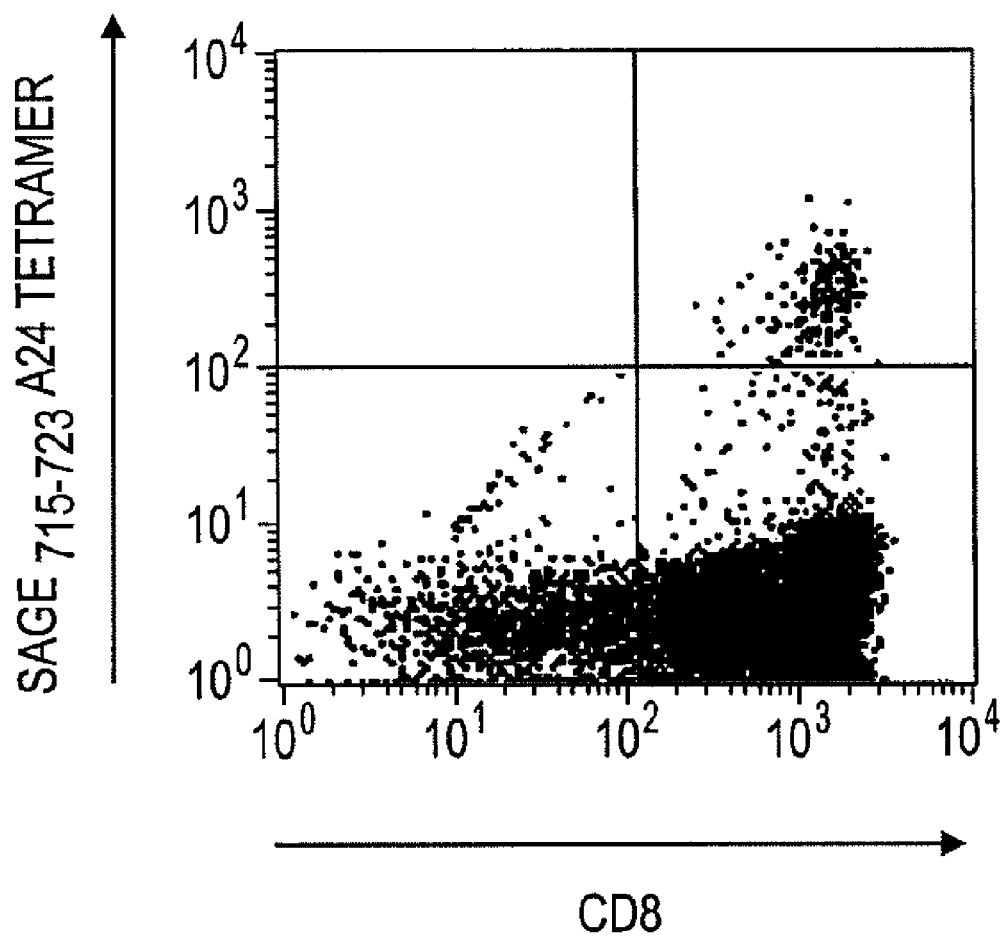

As a result, the resulting bulk CTL was positive in staining with SAGE$_{715-723}$ A24 tetramer, as shown in FIG. 4B. Accordingly, it was revealed that bulk CTLs contained CD8+ cells positive to SAGE$_{715-723}$ HLA-A24 tetramer.

T2A24 cells were then pulsed with SAGE$_{715-723}$ peptide. As the control, the cells were pulsed with HER2$_{63-71}$ peptide. Thereafter, the pulsed cells were subjected to ELISPOT assay. The results are shown in FIG. 4C.

Figure 4C:
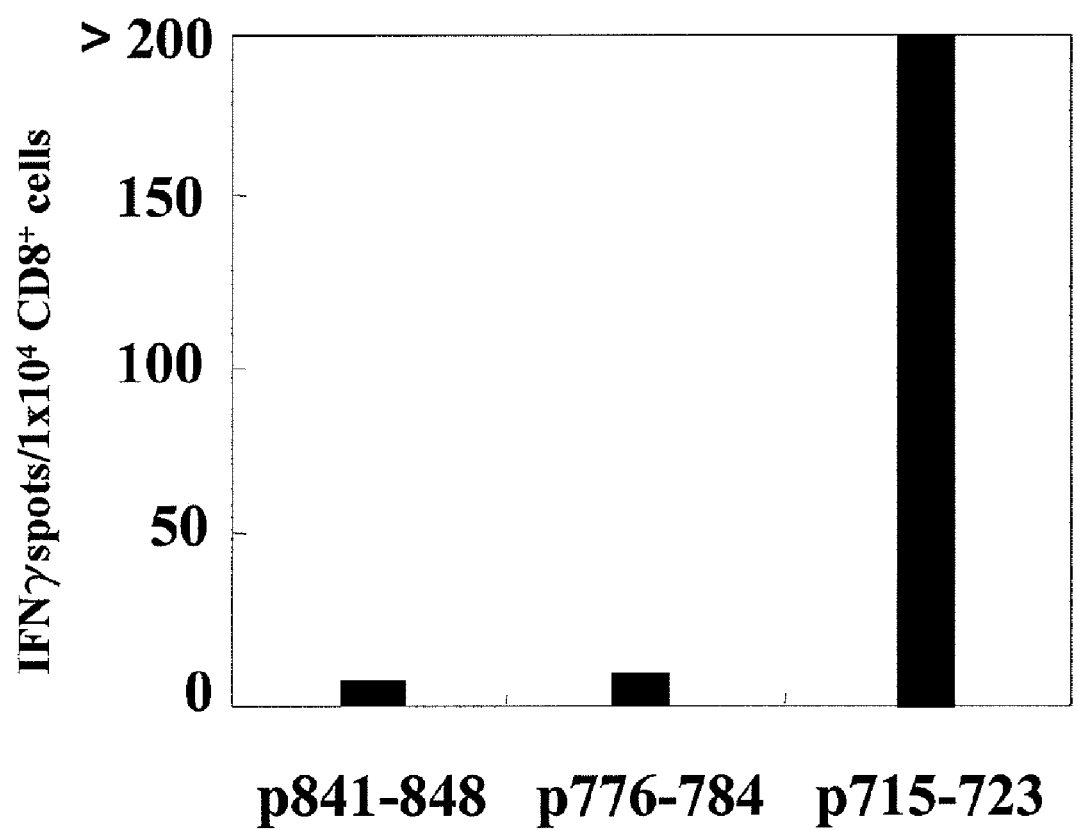

As a result, IFN-γ was released only when T2A24 pulsed with SAGE$_{715-723}$ peptide was used as the target cell, as shown in FIG. 4C.

Figure 5A:
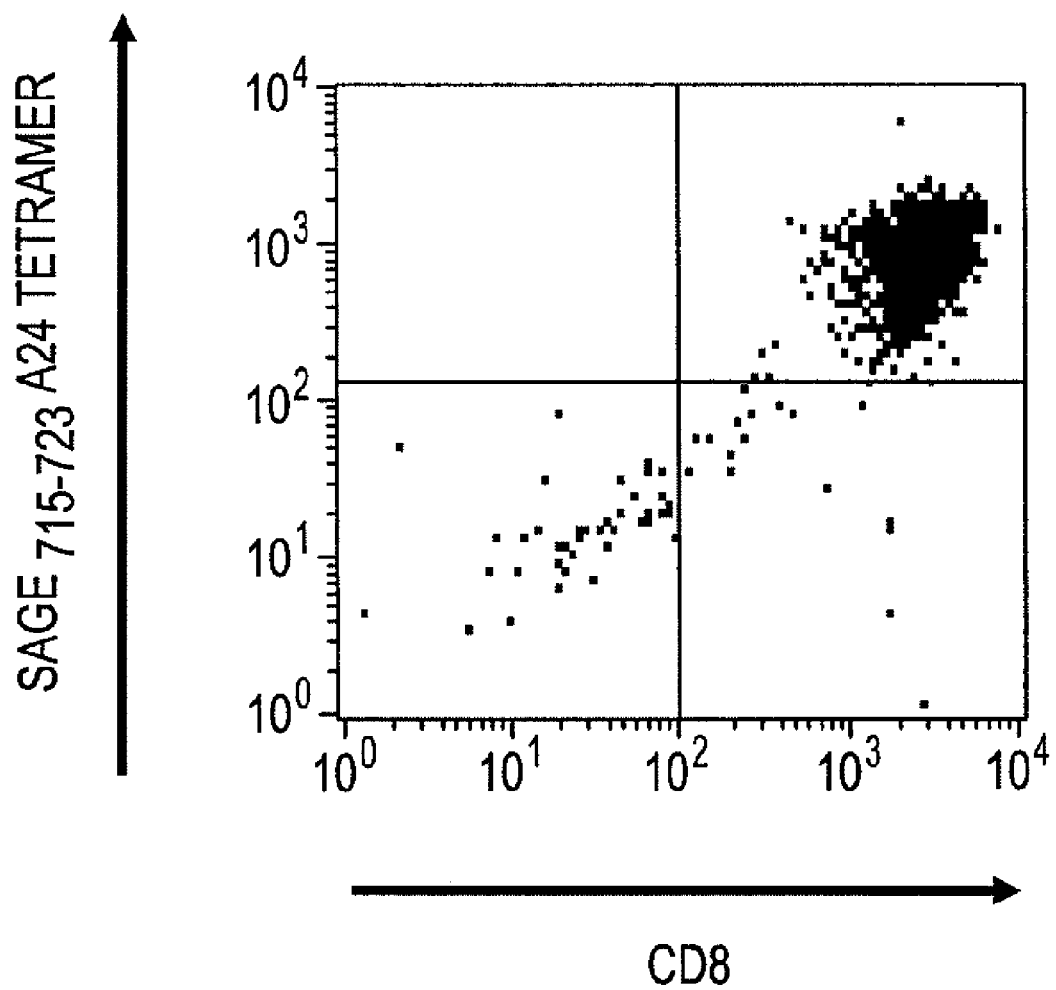
FIGS. 5A to 5C are graphs showing the results of presentation of S SAGE$_{715-723}$ peptide on cell surfaces together with HLA-A2402 after intracellular processing.
Figure 5B:
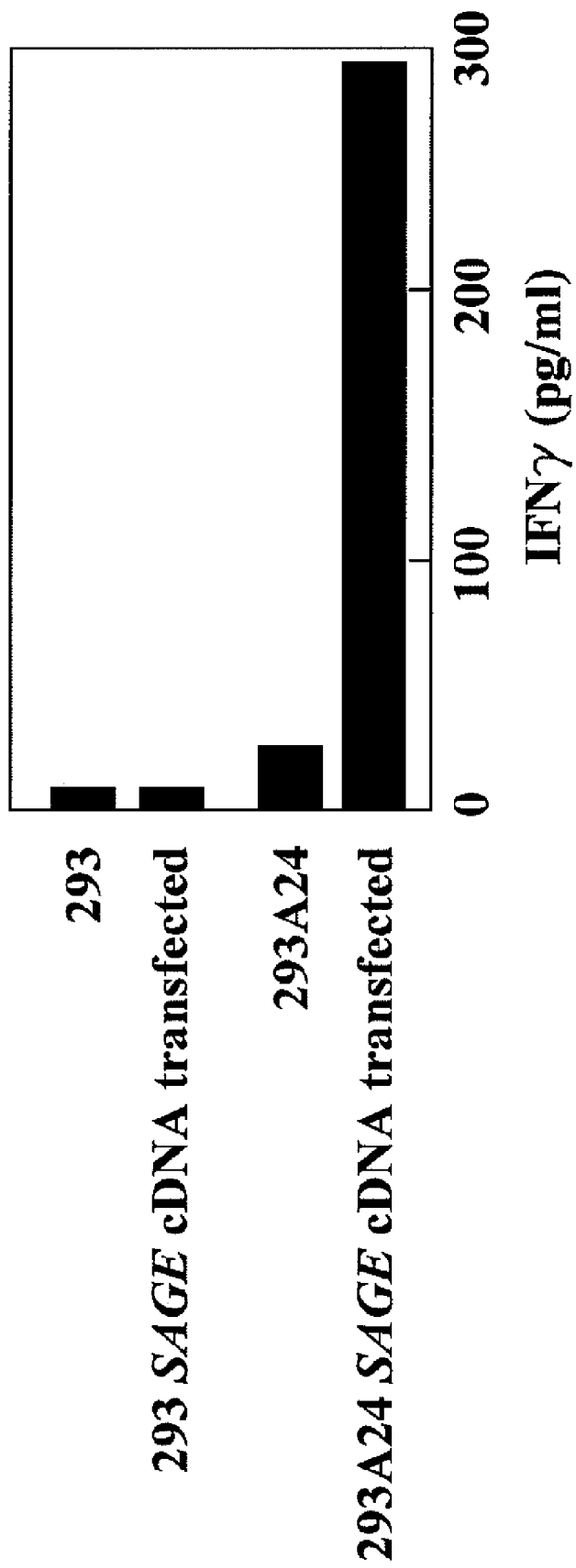
Figure 5C:
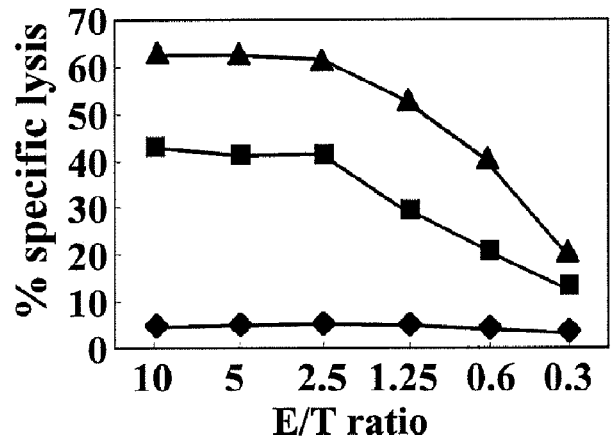
Figure 5C:
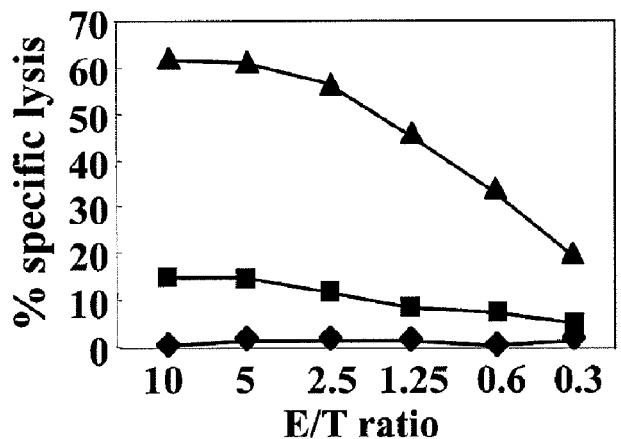
Figure 5C:
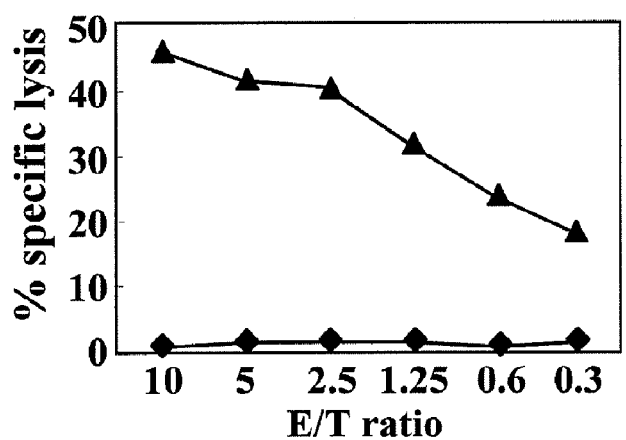
Figure 6A:
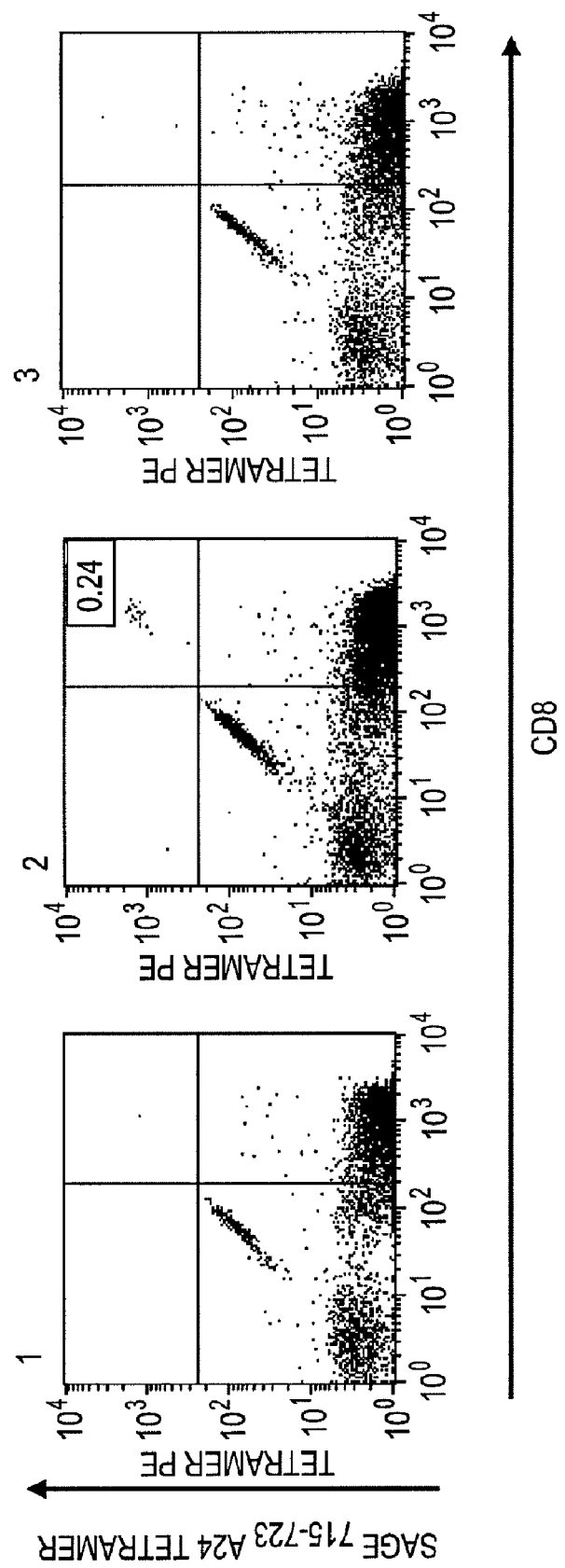
FIGS. 6A to 6D are graphs each showing one example of the results of detection of SAGE$_{715-723}$-specific precursor in healthy normal human PBMC.
Figure 6B:
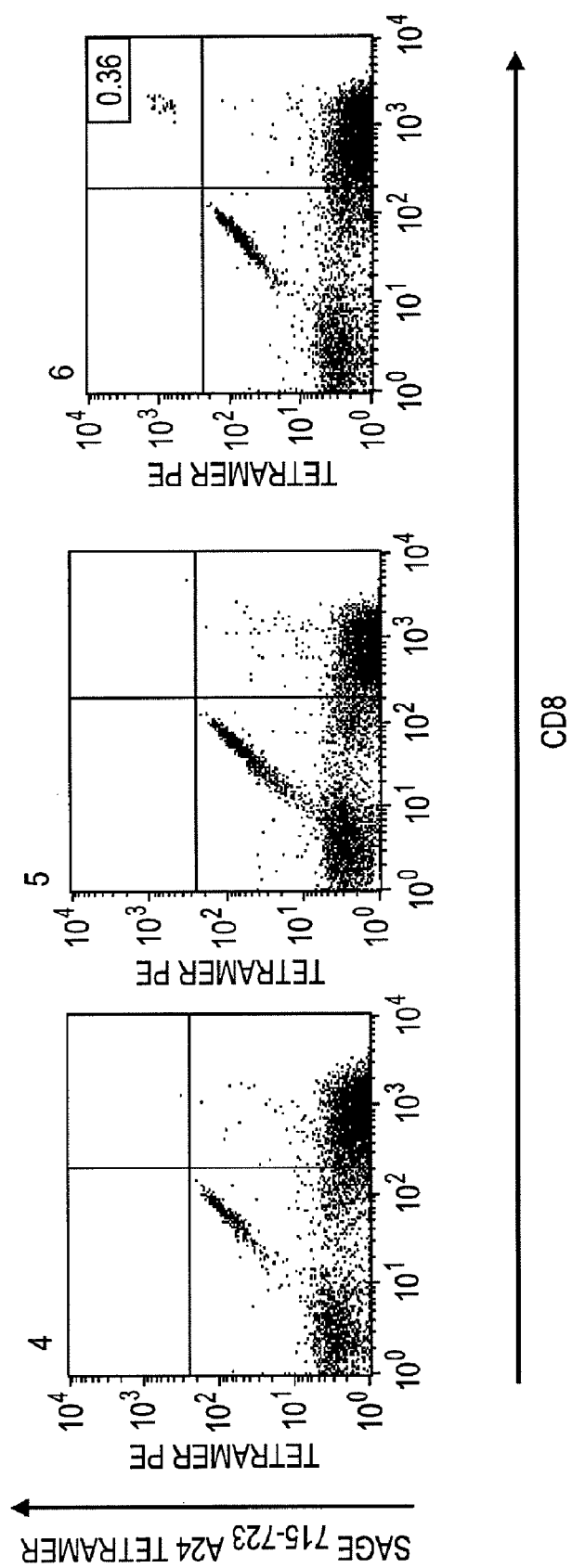
Figure 6C:
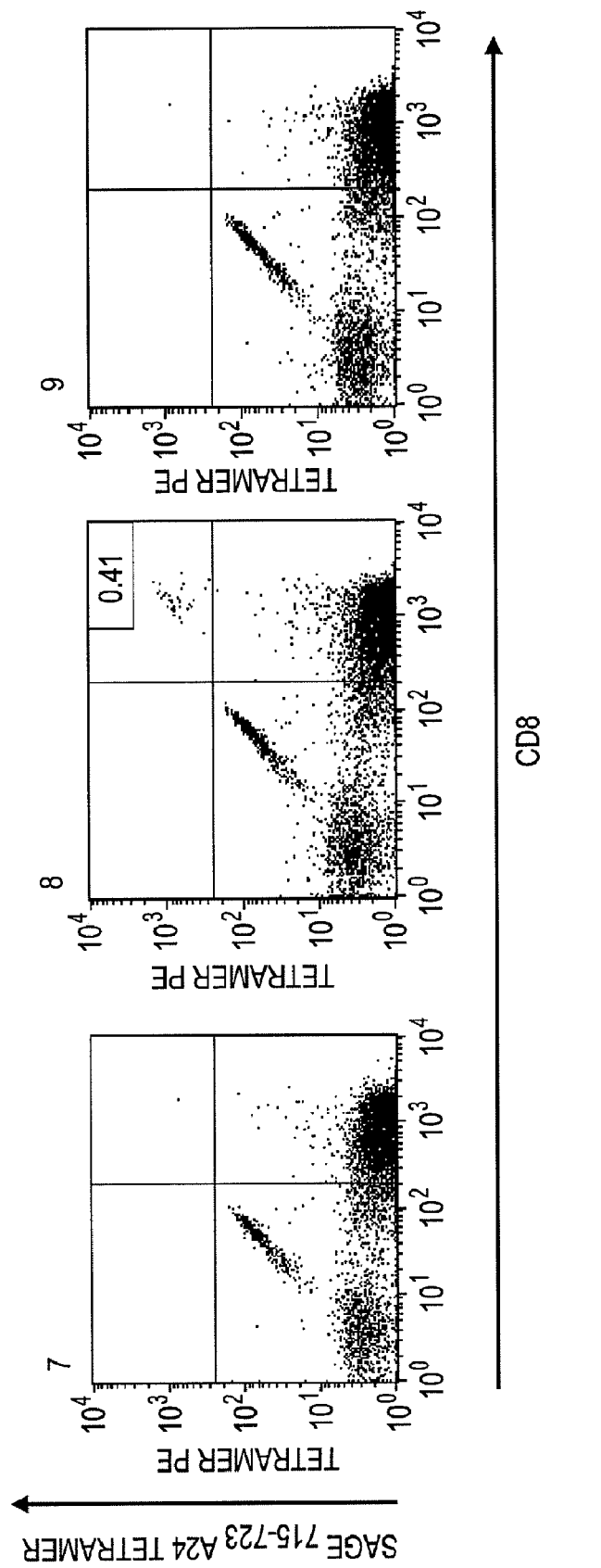
Figure 6D:
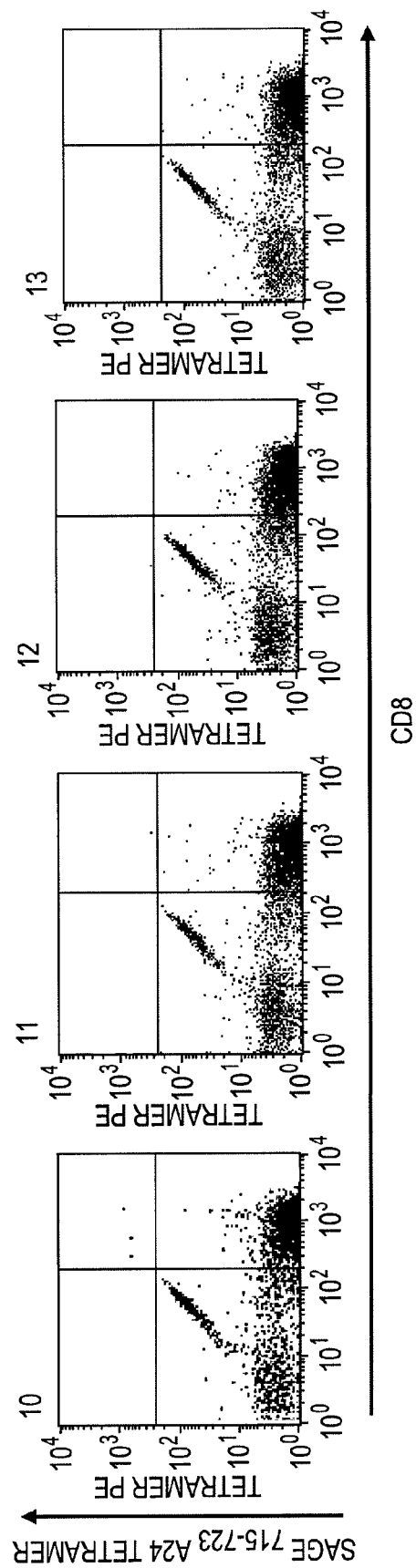

SAGE$_{715-723}$-specific HLA-A24 CTL cells #22 (#22 cells) were prepared by limiting dilution. The resulting #22 cells were analyzed by flow cytometry using SAGE$_{715-723}$ HLA-A24 tetramer and anti-CD8 antibody. The results are shown in FIG. 5A. The cytotoxicity by the #22 cells was also examined. The results are shown in FIG. 5C.

As a result, the #22 cells were positive to SAGE$_{715-723}$ HLA-A24 tetramer, as shown in FIG. 5A. When the #22 cells were co-cultured with 293-A2402 into which a plasmid carrying the full length of SAGE gene was introduced, the #22 cells secreted IFN-γ. The #22 cells (1×10⁴ cells), and 293A24 cells (1×10⁴ cells) transformed with SAGE cDNA, were cultured in a 96-well round plate for 18 hours. As a result, IFN-γ was released as shown in FIG. 5B. As shown in panels A and B in FIG. 5C, the #22 cells showed cytotoxicity to both K562A24 and R27A24. Here, both the K562A24 and R27A24 expressed HLA-A2402 and SAGE. Furthermore, as shown in panel C in FIG. 5C, there was specific cytotoxicity on A2402+LCL cells into which mRNA of SAGE gene was introduced.

EXAMPLE 3

SAGE$_{715-723}$-Specific CD8+ T Cells are Induced from A2402-Positive Healthy Normal Humans with High Probability In Vitro Induction of Human CTLs Using CD8− PBMC Pulsed with a Peptide The number 1×10⁷ of CD8-negative PBMC were pulsed with 10 μM peptide by incubation at room temperature for 1 hour and at 37° C. in 5% CO2 for 1 hour, in 200 μl RPMI1640 medium containing 25 mM Hepes, 10 wt % inactivated human AB-positive serum, 2 mM L-glutamine, 100 U/milliliter penicillin, and 100 μg/milliliter streptomycin. The resulting cells were used as antigen-presenting cells. The number 5×10⁵ of CD8+ T cells that were separated were then stimulated by incubation for from 10 to 12 days with 1×10⁶ cells of the peptide-pulsed CD8− PBMC. On Days 1, 4 and 7, half amount of the medium was exchanged with fresh one, and human IL-2 (20 IU/milliliter) and IL-7 (50 ng/milliliter) were added thereto. Culturing for induction was conducted in 200 μl RPMI1640 medium (containing 25 mM Hepes, 10 wt % inactivated human AB serum, 2 mM L-glutamine, 100 μg/milliliter penicillin, 100 μg/milliliter streptomycin).

It was examined whether an HLA-A2402-restricted SAGE$_{715-723}$-specific CTL was induced in vitro by once stimulating CD8+ cells from HLA-A2402-positive healthy normal volunteers, with CD8-negative PBMC pulsed with SAGE$_{715-723}$ peptide.

As a result, SAGE$_{715-723}$ HLA-A24 tetramer-positive T cells were detected in three out of six HLA-A2402+ healthy normal humans at 10 days after mixed lymphocyte reaction in vitro. FIGS. 6A to 6D each show one example of the analysis results.

EXAMPLE 4

Preparation of a Tetramer and Flow Cytometry Analysis

HLA-A2402 heavy chain and β2-microglobulin were expressed as an insoluble polymer in *Escherichia coli*. Here, in order to add a sequence serving as a substrate for biotinylating enzyme BirA to the C-terminal of the HLA-A2402 heavy chain, a corresponding polynucleotide was added to the nucleic acid encoding the HLA-A2402 heavy chain. A monomer HLA/β2-microglobulin/peptide complex was prepared in vitro by folding the insoluble polymer in the presence of MAGE-A4$_{143-151}$ peptide or SAGE$_{715-723}$. The resulting product was biotinylated with a recombinant BirA enzyme (manufactured by Avidity) and tetramerized with phycoerythrin-labelled streptavidin (manufactured by Molecular Probes Inc.) to give an MHC/peptide tetramer.

In staining, sensitized CD8+ T cells were reacted with 20 μg/milliliter tetramer at 37° C. for 30 minutes, and then reacted with a tricolor anti-CD8 monoclonal antibody (trade name, Caltag Laboratories, Burlingame, Calif., USA) on ice for 15 minutes. After washing, the stained cells were analyzed by flow cytometry (trade name: FACSCalibur, manufactured by Becton Dickinson, and Company). As a result, it was confirmed that the prepared tetramer was bound to the sensitized CD8+ T cells.

EQUIVALENTS

The present invention may be embodied in other specific forms without departing from the spirit or essential characteristics thereof. The present invention is therefore to be considered in all respects as illustrative and not restrictive. The scope of the invention is indicated by the appended claims rather than by the foregoing description. Furthermore, all changes which come within the meaning and range of equivalency of the claims are therefore intended to be embraced therein.

The invention claimed is:

1. An inducer of a cytotoxic T lymphocyte containing an isolated human major histo-compatibility antigen (HLA)-A24-restricted antigen peptide consisting of SEQ ID NO: 2 as an active ingredient.

2. A tetramer for detecting a T cell receptor possessed by a cytotoxic T lymphocyte, comprising an isolated human major histo-compatibility antigen (HLA)-A24-restricted antigen peptide consisting of SEQ ID NO: 2.

* * * * *

SEQUENCE LISTING

<160> NUMBER OF SEQ ID NOS: 17

<210> SEQ ID NO 1
<211> LENGTH: 9
<212> TYPE: PRT
<213> ORGANISM: Homo sapiens

<400> SEQUENCE: 1

Asn Tyr Lys Arg Cys Phe Pro Val Ile
1               5

<210> SEQ ID NO 2
<211> LENGTH: 9
<212> TYPE: PRT
<213> ORGANISM: Homo sapiens

<400> SEQUENCE: 2

Leu Tyr Ala Thr Val Ile His Asp Ile
1               5

<210> SEQ ID NO 3
<211> LENGTH: 9
<212> TYPE: PRT
<213> ORGANISM: Homo sapiens

<400> SEQUENCE: 3

Asn Tyr Glu Arg Ile Phe Ile Leu Leu
1               5

<210> SEQ ID NO 4
<211> LENGTH: 9
<212> TYPE: PRT
<213> ORGANISM: Homo sapiens

<400> SEQUENCE: 4

Leu Tyr Lys Pro Asp Ser Asn Glu Phe
1               5

<210> SEQ ID NO 5
<211> LENGTH: 9
<212> TYPE: PRT
<213> ORGANISM: Homo sapiens

<400> SEQUENCE: 5

Gln Tyr Ala Ala Val Thr His Asn Ile
1               5

<210> SEQ ID NO 6
<211> LENGTH: 9
<212> TYPE: PRT
<213> ORGANISM: Homo sapiens

<400> SEQUENCE: 6

Thr Tyr Asn Val Pro Glu Glu Lys Met
1               5

<210> SEQ ID NO 7
<211> LENGTH: 9
<212> TYPE: PRT
<213> ORGANISM: Homo sapiens

<400> SEQUENCE: 7

Val Tyr Gly Glu Pro Arg Lys Leu Leu
1               5

<210> SEQ ID NO 8
<211> LENGTH: 9
<212> TYPE: PRT
<213> ORGANISM: Homo sapiens

<400> SEQUENCE: 8

Glu Phe Leu Trp Gly Pro Arg Ala Leu
1               5

<210> SEQ ID NO 9
<211> LENGTH: 9
<212> TYPE: PRT
<213> ORGANISM: Homo sapiens

<400> SEQUENCE: 9

Ile Phe Gly Lys Ala Ser Glu Ser Leu
1               5

<210> SEQ ID NO 10
<211> LENGTH: 9

```
<212> TYPE: PRT
<213> ORGANISM: Homo sapiens

<400> SEQUENCE: 10

Lys Val Asp Glu Leu Ala His Phe Leu
1               5

<210> SEQ ID NO 11
<211> LENGTH: 9
<212> TYPE: PRT
<213> ORGANISM: Homo sapiens

<400> SEQUENCE: 11

Ser Tyr Val Lys Val Leu Glu His Val
1               5

<210> SEQ ID NO 12
<211> LENGTH: 9
<212> TYPE: PRT
<213> ORGANISM: Homo sapiens

<400> SEQUENCE: 12

Lys Tyr Arg Ala Lys Glu Leu Val Thr
1               5

<210> SEQ ID NO 13
<211> LENGTH: 9
<212> TYPE: PRT
<213> ORGANISM: Homo sapiens

<400> SEQUENCE: 13

Lys Thr Glu Leu Leu Ile Ile Val Leu
1               5

<210> SEQ ID NO 14
<211> LENGTH: 9
<212> TYPE: PRT
<213> ORGANISM: Homo sapiens

<400> SEQUENCE: 14

Ala Tyr Pro Ser Leu Arg Glu Ala Ala
1               5

<210> SEQ ID NO 15
<211> LENGTH: 9
<212> TYPE: PRT
<213> ORGANISM: Homo sapiens

<400> SEQUENCE: 15

Ser Ser Pro Leu Val Pro Gly Thr Leu
1               5

<210> SEQ ID NO 16
<211> LENGTH: 9
<212> TYPE: PRT
<213> ORGANISM: Epstein-Barr virus

<400> SEQUENCE: 16

Arg Tyr Ser Ile Phe Phe Asp Tyr Met
1               5

<210> SEQ ID NO 17
<211> LENGTH: 9
<212> TYPE: PRT
<213> ORGANISM: Homo sapiens
```

```
<400> SEQUENCE: 17

Thr Tyr Leu Pro Thr Asn Ala Ser Leu
1               5
```